(12) United States Patent
Bailey et al.

(10) Patent No.: US 7,568,836 B2
(45) Date of Patent: *Aug. 4, 2009

(54) MOBILE COMPUTERIZED TOMOGRAPHY (CT) IMAGING SYSTEM WITH OFF-CENTER X-RAY BEAM

(75) Inventors: Eric M. Bailey, Hampton, NH (US); Andrew P. Tybinkowski, Boxford, MA (US); Lidia Nemirovsky, Salem, MA (US)

(73) Assignee: NeuroLogica Corp., Danvers, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/653,706

(22) Filed: Jan. 16, 2007

(65) Prior Publication Data

US 2007/0195938 A1    Aug. 23, 2007

Related U.S. Application Data

(63) Continuation-in-part of application No. 11/193,941, filed on Jul. 29, 2005, now Pat. No. 7,175,347, and a continuation-in-part of application No. 11/399,283, filed on Apr. 6, 2006.

(60) Provisional application No. 60/670,164, filed on Apr. 11, 2005, provisional application No. 60/593,001, filed on Jul. 30, 2004.

(51) Int. Cl.
*H05G 1/02*     (2006.01)
*H05G 1/00*     (2006.01)

(52) U.S. Cl. ............................. 378/198; 378/4; 378/20

(58) Field of Classification Search .................... 378/4, 378/8, 15, 20, 193–198, 205–208
See application file for complete search history.

(56) References Cited

U.S. PATENT DOCUMENTS

| 3,603,975 | A | | 9/1971 | Gordon |
| 4,501,009 | A | * | 2/1985 | Abele .......................... 378/19 |
| 4,870,671 | A | | 9/1989 | Hershyn |
| 5,887,047 | A | | 3/1999 | Bailey et al. |
| 5,982,843 | A | | 11/1999 | Bailey et al. |

(Continued)

*Primary Examiner*—Irakli Kiknadze
(74) *Attorney, Agent, or Firm*—Pandiscio & Pandiscio

(57) ABSTRACT

A mobile CT imaging system comprising:
   a housing having a center opening; and
   a CT imaging unit mounted to the housing, wherein the CT imaging unit is adapted to scan anatomical objects located within the center opening and generate images of the same, wherein the CT imaging unit comprises:
      a rotatable drum assembly disposed within the housing, concentric with the center opening;
      an X-ray tube mounted on the rotatable drum assembly and configured to emit an X-ray beam; and
      an X-ray detector mounted on the rotatable drum assembly in alignment with the X-ray beam;
      wherein the X-ray beam is disposed in an "off-center" configuration, adjacent to an entrance of the center opening.

A CT imaging system comprising:
   a housing having a center opening larger than the head of a patient and smaller than the shoulders of a patient; and
   a CT imaging unit mounted to the housing, wherein the CT imaging unit is adapted to scan anatomical objects located within the center opening and generate images of the same, wherein the CT imaging unit is configured to scan substantially the full range of the anatomy placed within the center opening.

14 Claims, 29 Drawing Sheets

U.S. PATENT DOCUMENTS

| | | |
|---|---|---|
| 6,108,396 A | 8/2000 | Bechwati et al. |
| 6,256,404 B1 | 7/2001 | Gordon et al. |
| 6,256,528 B1 * | 7/2001 | Zonneveld et al. .......... 600/425 |
| 6,285,028 B1 | 9/2001 | Yamakawa |
| 6,396,902 B2 | 5/2002 | Tybinkowski et al. |
| 6,459,767 B1 | 10/2002 | Boyer |
| 6,522,721 B1 | 2/2003 | Lustberg |
| 6,813,374 B1 | 11/2004 | Karimi et al. |
| 6,857,778 B2 | 2/2005 | Mun et al. |
| 7,175,347 B2 | 2/2007 | Tybinkowski et al. |
| 2003/0235265 A1 * | 12/2003 | Clinthorne et al. ............. 378/4 |
| 2005/0135560 A1 * | 6/2005 | Dafni et al. ................. 378/101 |
| 2006/0251218 A1 | 11/2006 | Tybinkowski et al. |
| 2007/0183588 A1 | 8/2007 | Bailey et al. |
| 2007/0183589 A1 | 8/2007 | Tybinkowski et al. |
| 2007/0195938 A1 | 8/2007 | Bailey et al. |

* cited by examiner

MOBILE COMPUTERIZED TOMOGRAPHY (CT) IMAGING SYSTEM WITH OFF-CENTER X-RAY BEAM

REFERENCE TO PENDING PRIOR PATENT APPLICATIONS

This patent application is:

(i) a continuation-in-part of pending prior U.S. patent application Ser. No. 11/193,941, filed Jul. 29, 2005 now U.S. Pat. No. 7,175,347 by Andrew P. Tybinkowski et al. for ANATOMICAL IMAGING SYSTEM WITH CENTIPEDE DRIVE which patent application in turn claims benefit of:

(a) prior U.S. Provisional Patent Application Ser. No. 60/670,164, filed Apr. 11, 2005 by Andrew P. Tybinkowski et al. for ANATOMICAL IMAGING SYSTEM WITH CENTIPEDE DRIVE; and (b) prior U.S. Provisional Patent Application Ser. No. 60/593,001, filed Jul. 30, 2004 by Bernard Gordon et al. for ANATOMICAL SCANNING SYSTEM; and (ii) a continuation-in-part of pending prior U.S. patent application Ser. No. 11/399,283, filed Apr. 06, 2006 by Andrew P. Tybinkowski et al. for COMPUTERIZED TOMOGRAPHY (CT) IMAGING SYSTEM WITH MONOBLOCK X-RAY TUBE ASSEMBLY.

The four above-identified patent applications are hereby incorporated herein by reference.

FIELD OF THE INVENTION

This invention relates to anatomical imaging systems in general, and more particularly to Computerized Tomography (CT) imaging systems.

BACKGROUND OF THE INVENTION

Strokes are currently the third leading cause of death in the United States, causing approximately 177,000 deaths per year, and strokes are currently the number one cause of long-term disability in the United States, currently affecting nearly 5 million people. Strokes are caused by an abrupt interruption of the blood supply to the brain or spinal cord, thereby depriving the tissue of oxygen and resulting in tissue damage.

Strokes typically occur in one of two forms: (i) hemorrhagic stokes, which occur with the rupture of a blood vessel; and (ii) ischemic strokes, which occur with the obstruction of a blood vessel.

Rapid diagnosis is a key component of stroke treatment. This is because the treatment for an ischemic stroke may be contra-indicated for the treatment for a hemorrhagic stroke and, furthermore, the effectiveness of a particular treatment may be time-sensitive. More particularly, the current preferred treatment for an acute ischemic stroke, i.e., the administration of tPA to eliminate blood clots, is contra-indicated for a hemorrhagic stroke. Furthermore, the clinical data suggests that the medication used to treat ischemic strokes (i.e., tPA) is most effective if it is administered within 3 hours of the onset of the stroke. However, current diagnosis times, i.e., the time needed to identify that the patient is suffering from a stroke and to identify the hemorrhagic or ischemic nature of the stroke, frequently exceeds this 3 hour window. As a result, only a fraction of current ischemic stroke victims are timely treated with tPA.

Imaging is generally necessary to properly diagnose (and hence properly treat) a stroke. More particularly, imaging is generally necessary to: (i) distinguish strokes from other medical conditions; (ii) distinguish between the different types of strokes (i.e., hemorrhagic or ischemic); and (iii) determine appropriate treatments (e.g., the administration of tPA in the case of an ischemic stroke).

Computerized Tomography (CT) has emerged as the key imaging modality in the diagnosis of strokes. CT imaging systems generally operate by directing X-rays into the body from a variety of positions, detecting the X-rays passing through the body, and then processing the detected X-rays so as to build a computer model of the patient's anatomy. This computer model can then be visualized so as to provide images of the patient's anatomy. It has been found that such CT scanning, including non-enhanced CT scanning, CT angiography scanning and CT perfusion scanning, is able to provide substantially all of the information needed to effectively diagnose (and hence properly treat) a stroke.

Unfortunately, in practice, the CT imaging system is typically located in the hospital's radiology department and the patient is typically received in the hospital's emergency room, and the "round-trip" time between the emergency room and the radiology department can frequently involve substantial delays, even in the best of hospitals. As a result, the time spent in transporting the patient from the emergency room to the radiology department and then back again can consume critical time which can compromise proper treatment of the patient (e.g., it can prevent ischemic stroke victims from being timely treated with tPA).

Thus, there is an urgent need for a new and improved CT imaging system which is particularly well suited for use in stroke applications. More particularly, there is an urgent need for a small, mobile CT imaging system which can be pre-positioned in the emergency room and moved to the patient so that the patient can be scanned at their current location, thus effectively eliminating "round-trip" delays and dramatically reducing the time needed to properly diagnose the patient. It is also important that the CT imaging system be relatively inexpensive, so as to facilitate its rapid proliferation and widespread use, e.g., pre-positioning in substantially all hospital emergency rooms and wide availability in outlying, low-volume settings (e.g., rural hospitals, ships, etc.).

In this respect it should also be appreciated that current CT imaging systems are generally quite large. This is due to (i) the general nature of CT imaging systems, and (ii) the anatomy that the current CT imaging systems are designed to scan.

More particularly, and looking now at FIGS. 1 and 2, current CT imaging systems generally comprise a housing A having a center opening B and enclosing a rotating drum assembly C, an X-ray tube assembly D adapted to emit X-rays, and an X-ray detector assembly E adapted to detect X-rays. X-ray tube assembly D and X-ray detector assembly E are mounted to rotating drum assembly C about center opening B, in diametrically-opposing relation, such that the X-ray beam F (generated by X-ray tube assembly D and detected by X-ray detector assembly E) is passed through the interior of the drum assembly C (i.e., across center opening B), and hence is passed through patient anatomy disposed within the interior of rotating drum assembly C (i.e., patient anatomy disposed within center opening B). Furthermore, since X-ray tube assembly D and X-ray detector assembly E are mounted on rotating drum assembly C so that they are rotated concentrically about the axis of rotating drum assembly C, X-ray beam F will be passed through the patient's anatomy along a full range of radial positions. As a result, by moving the patient longitudinally through center opening B while passing X-ray beam F through the anatomy along a range of radial positions, the CT imaging system can create the desired computer model of the scanned anatomy. Thus it will be appreciated that CT imaging systems must be large enough to fit, within the interior of drum assembly C, the patient anatomy which is to be scanned. Since conventional CT imaging systems are generally designed to scan any portion of the patient's anatomy, such CT imaging systems must have a center opening large enough to accept the torso of the patient B. Accordingly, conventional CT imaging systems are generally of substantial size.

Furthermore, since X-ray tube assembly D and X-ray detector assembly E are typically of substantial size and complexity (e.g., X-ray tube assembly D generally requires substantial power to penetrate the torso, and typically includes substantial power elements, cooling systems, etc., and X-ray detector assembly E typically includes substantial detector structure, etc.), and since X-ray tube assembly D and X-ray detector assembly E must remain fixed in position relative to one another with a high degree of precision even as drum assembly C is rotated at substantial speeds, X-ray tube assembly D and X-ray detector assembly E are typically mounted to rotating drum assembly C so that each assembly is concentric about the mid-point of the depth of the drum assembly. This arrangement minimizes cantilevering and provides the most stable mounting of X-ray tube assembly D and X-ray detector assembly E to rotating drum assembly C. Thus, with conventional CT imaging systems, X-ray beam F is positioned at the mid-point of the depth of the drum assembly. For purposes of the present invention, conventional CT imaging systems can be considered to have an "on-center" X-ray beam configuration.

The aforementioned construction of conventional CT imaging systems generally does not present a problem when the CT imaging system is a large, fixed-position installation designed to scan any portion of the patient's anatomy. However, such a construction presents a serious problem when trying to build a small, mobile CT imaging system intended to scan only the head of the patient, e.g., a potential stroke victim. This is because CT imaging systems having a center opening large enough to receive the torso of a patient must also have an overall size which makes it impractical to move the CT imaging system about the hospital.

Furthermore, it is not possible to solve the aforementioned problem by simply reducing the size of the CT imaging system so that it has a center opening just large enough to receive only the head of the patient. This is because the shoulders of the patient limit the extent to which the patient's head can be advanced into the center opening of the CT scanner. Thus, the conventional approach of locating the X-ray beam at the mid-point of the depth of the drum assembly (i.e., the aforementioned "on-center" configuration) prevents the lower portion of the head from being passed through the "on-center" x-ray beam. See FIG. 2A. This can be unacceptable for many potential stroke victims, who may be affected in the lower portion of the brain or the upper portion of the neck.

Thus, there is a need for a new and improved approach for positioning the X-ray tube assembly and the X-ray detector assembly within a CT imaging system, so as to facilitate the provision of a mobile (i.e., small) CT imaging system which can scan the entire head of a patient.

SUMMARY OF THE INVENTION

In accordance with the present invention, there is provided a novel approach for positioning the X-ray tube assembly and the X-ray detector assembly within a CT imaging system, so as to facilitate the provision of a mobile (i.e., small) CT imaging system which can scan the entire head of a patient.

And there is provided a novel mobile CT imaging system having a significantly reduced size but which is still capable of scanning substantially the full range of the anatomy placed within the center opening of the CT imaging system, e.g., the entire head and upper neck of a patient.

In one form of the invention, there is provided a mobile CT imaging system comprising:

a housing having a center opening; and a CT imaging unit mounted to the housing, wherein the CT imaging unit is adapted to scan anatomical objects located within the center opening and generate images of the same, wherein the CT imaging unit comprises:

a rotatable drum assembly disposed within the housing, concentric with the center opening;

an X-ray tube mounted on the rotatable drum assembly and configured to emit an X-ray beam; and an X-ray detector mounted on the rotatable drum assembly in alignment with the X-ray beam;

wherein the X-ray beam is disposed in an "off-center" configuration, adjacent to an entrance of the center opening.

In another form of the invention, there is provided a CT imaging system comprising:

a housing having a center opening larger than the head of a patient and smaller than the shoulders of a patient; and a CT imaging unit mounted to the housing, wherein the CT imaging unit is adapted to scan anatomical objects located within the center opening and generate images of the same, wherein the CT imaging unit is configured to scan substantially the full range of the anatomy placed within the center opening.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein.

DETAILED DESCRIPTION OF THE PREFERRED EMBODIMENTS

The Mobile CT Imaging System In General

Figure 1:
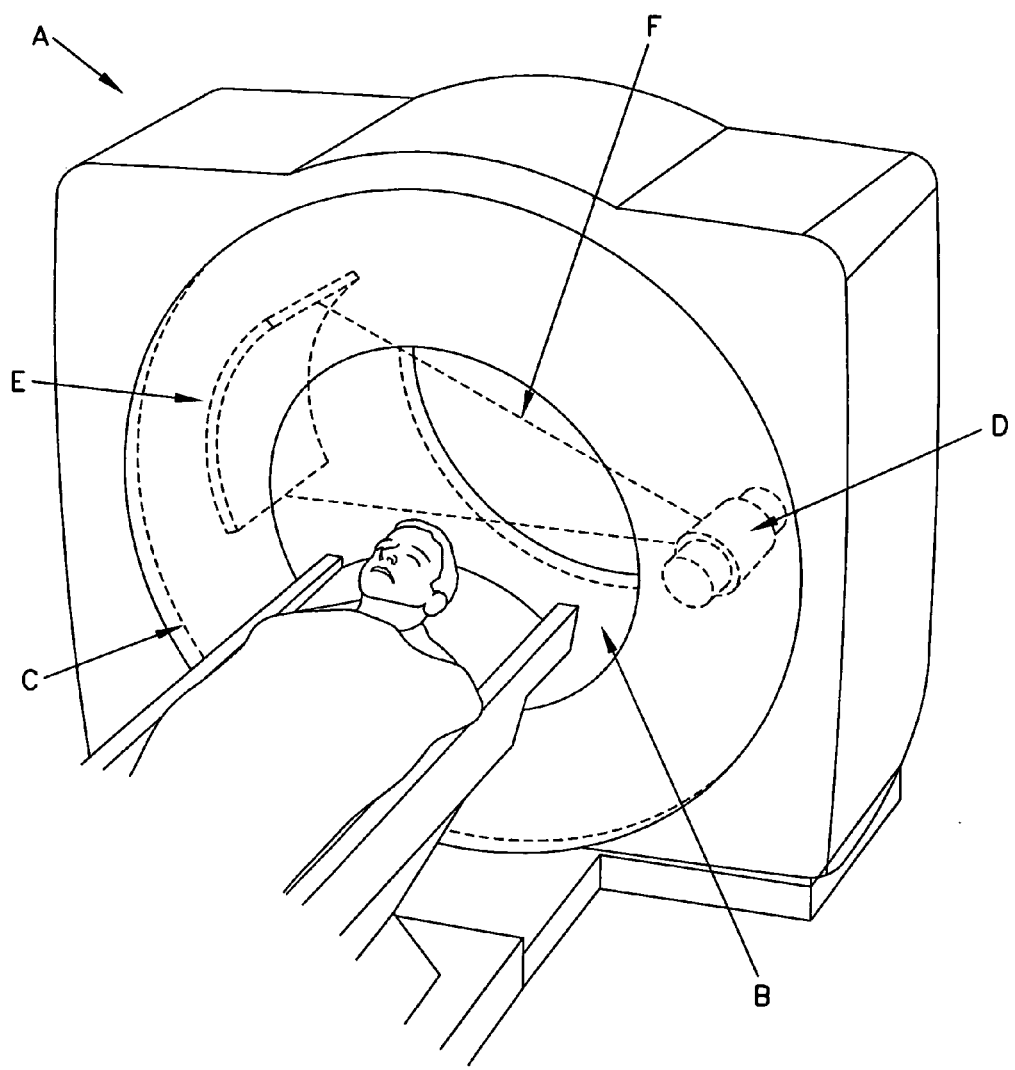
FIG. 1 is a schematic external view of a conventional CT imaging system.
Figure 2:
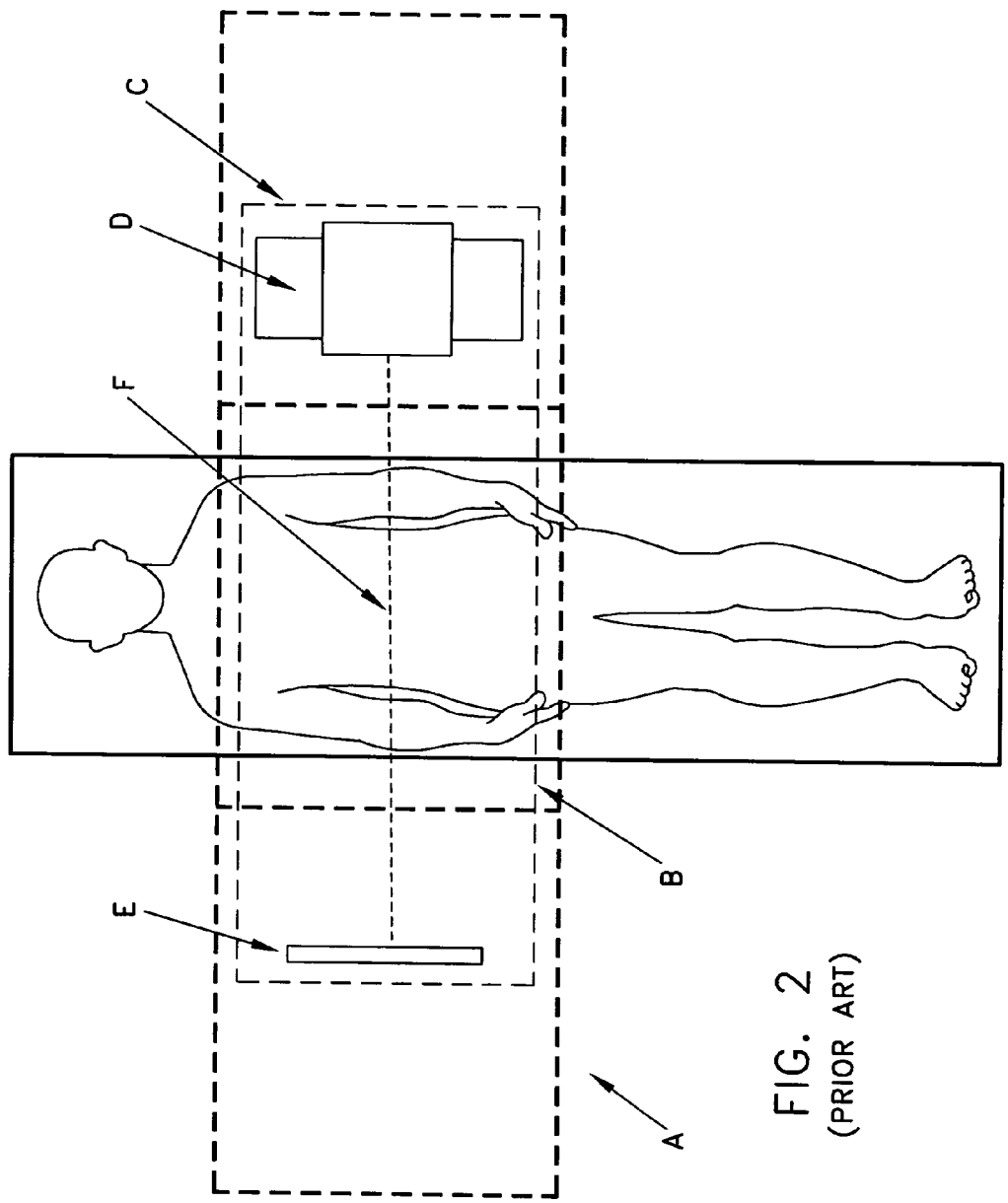
FIG. 2 is a schematic top view of the conventional CT imaging system shown in FIG. 1.
Figure 2A:
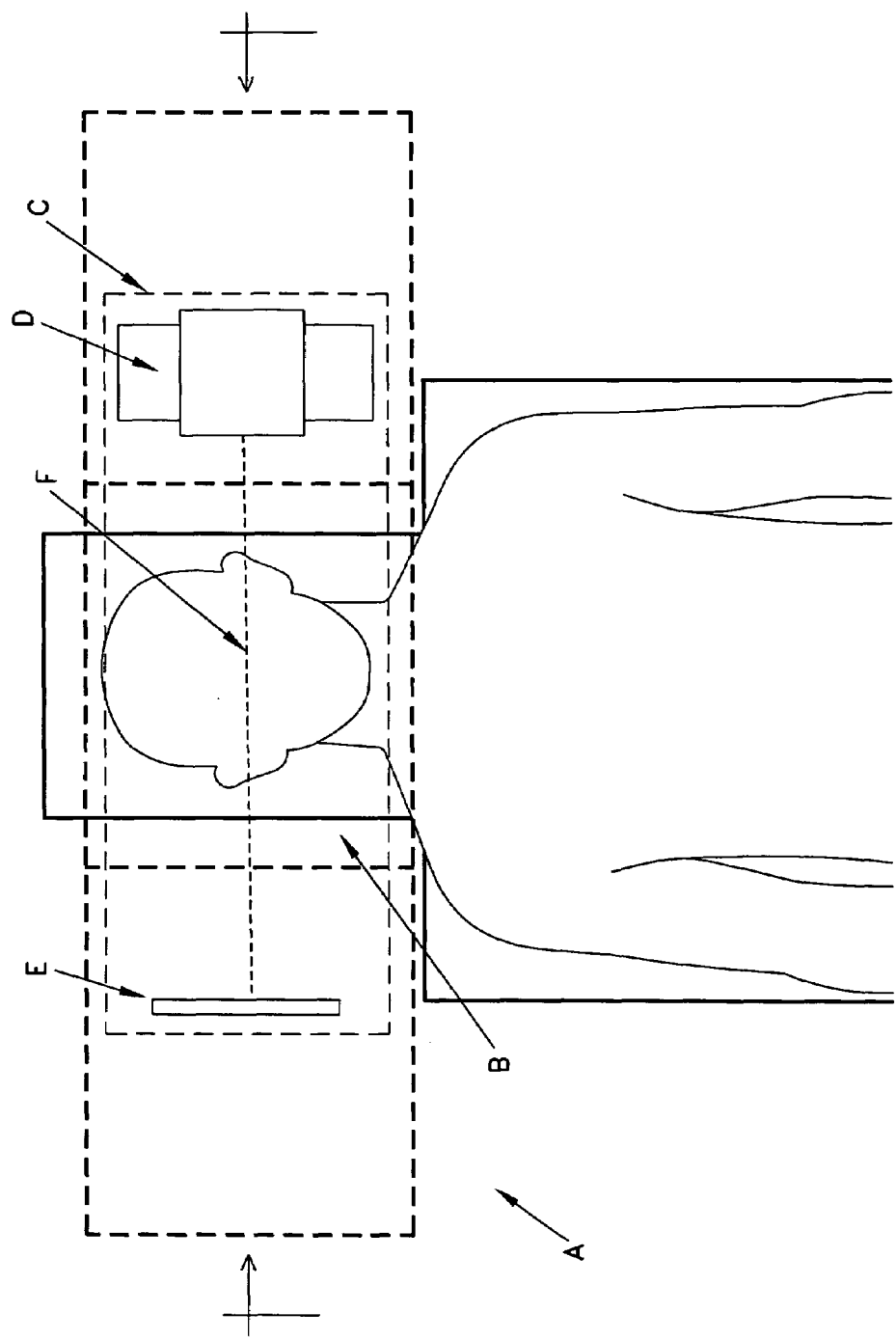
FIG. 2A is a schematic top view of the conventional CT imaging system shown in FIG. 1, but reduced in size so as to have a center opening just large enough to receive the head of a patient.
Figure 3:
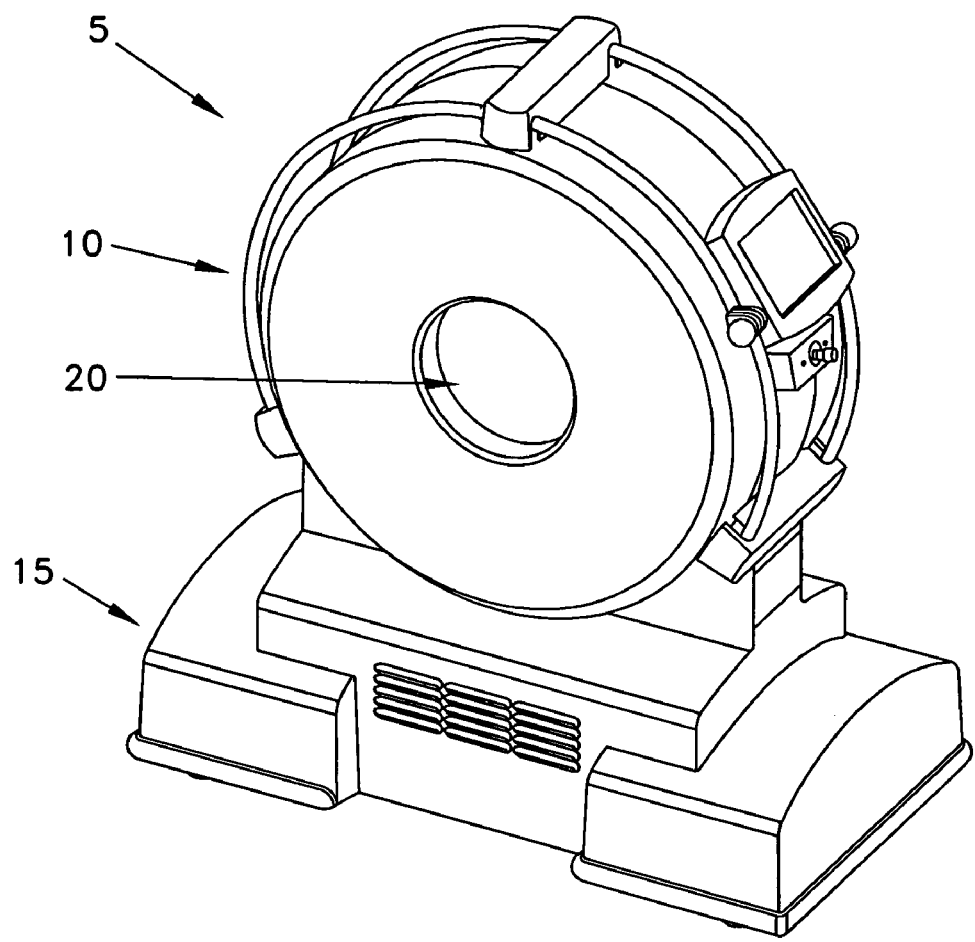
FIGS. 3, 4 and 5 are schematic views of a novel CT imaging system formed in accordance with the present invention.
Figure 4:
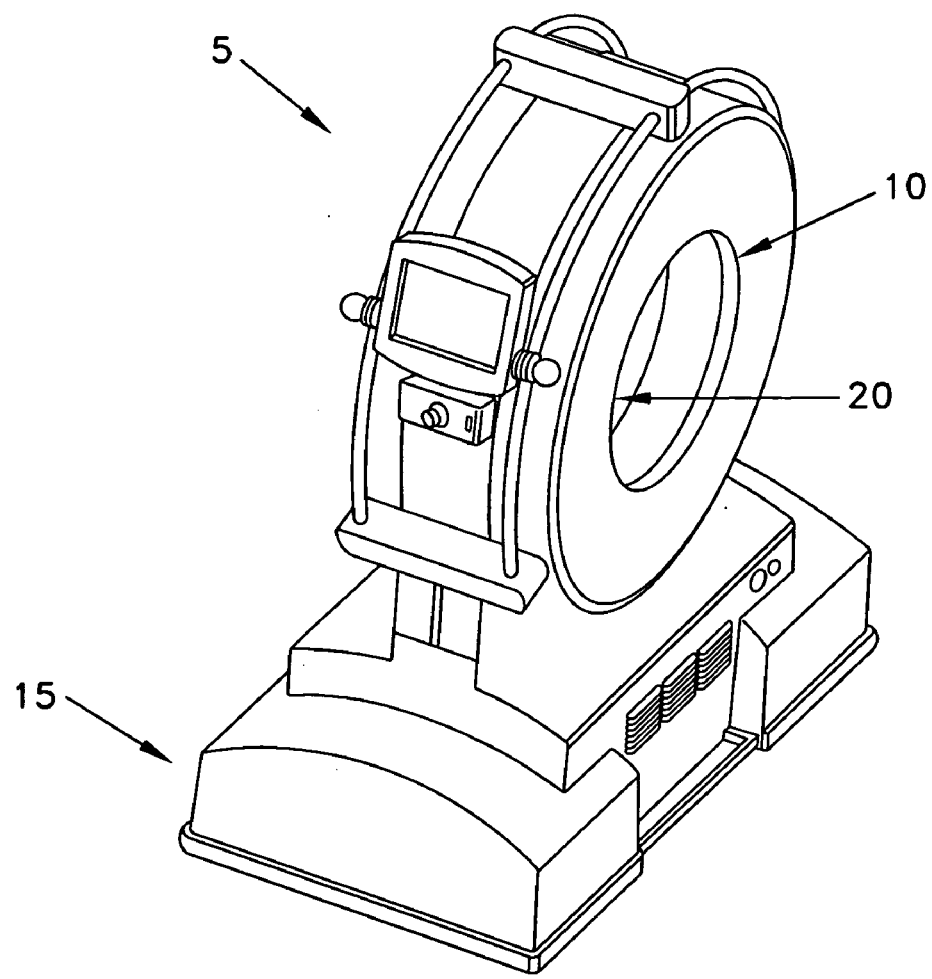
Figure 5:
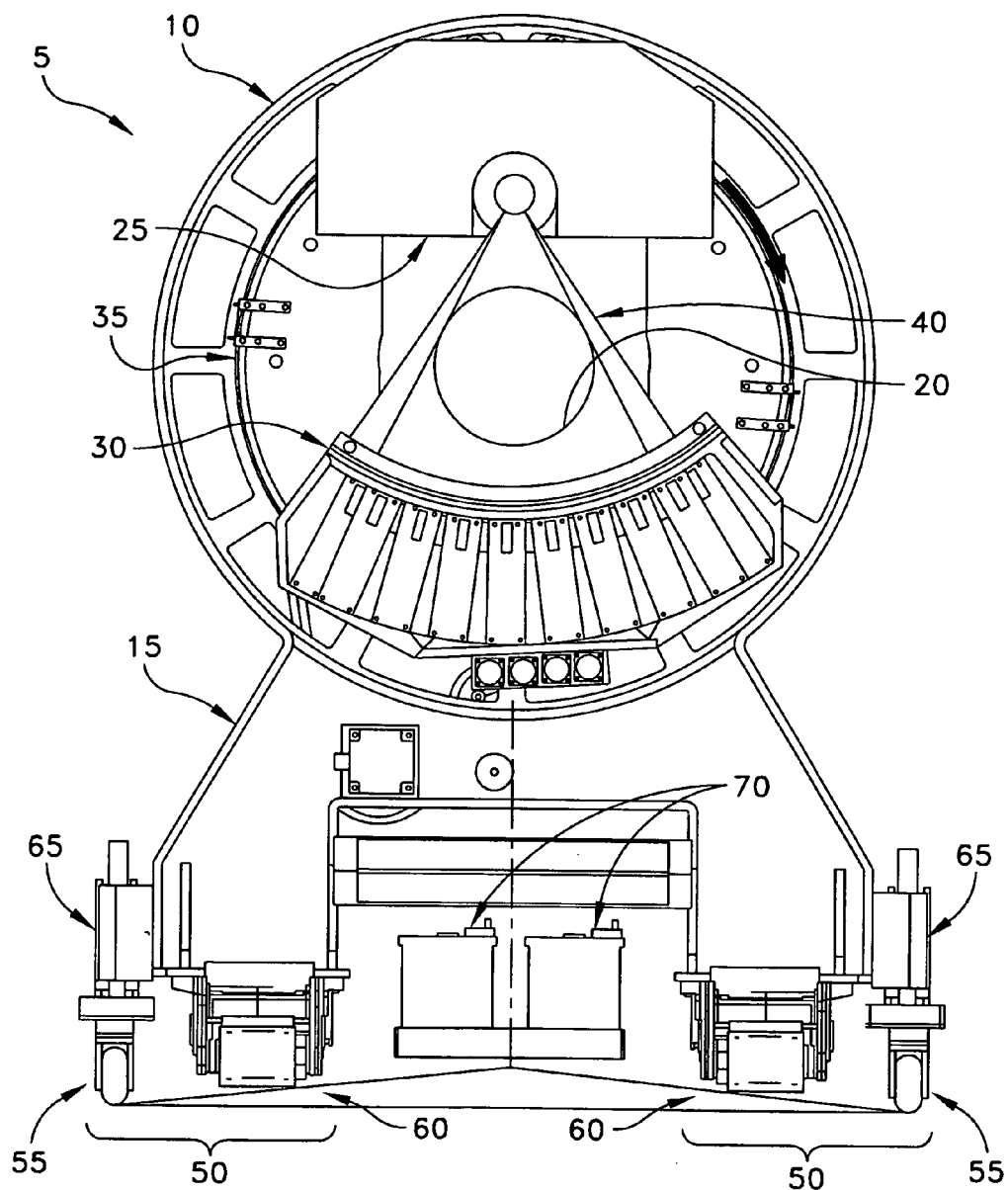

Looking now at FIGS. 3-5, there is shown a novel mobile CT imaging system 5 formed in accordance with the present invention. Mobile CT imaging system 5 generally comprises a torus 10 which is supported by a base 15. Torus 10 and base 15 together comprise a frame for mobile CT imaging system 5. A center opening 20 is formed in torus 10. Center opening 20 receives the patient anatomy which is to be scanned, i.e., the head of the patient when mobile CT imaging system 5 is to be used in stroke applications.

As seen in FIG. 5, torus 10 generally comprises a X-ray tube assembly 25, an X-ray detector assembly 30, and a rotating drum assembly 35. X-ray tube assembly 25 and X-ray detector assembly 30 are mounted to rotating drum assembly 35 in diametrically-opposing relation, such that the X-ray beam 40 (generated by X-ray tube assembly 25 and detected by X-ray detector assembly 30) is passed through patient anatomy disposed in center opening 20. Furthermore, since X-ray tube assembly 25 and X-ray detector assembly 30 are mounted on rotating drum assembly 35 so that they are rotated concentrically about center opening 20, X-ray beam 40 will be passed through the patient's anatomy along a full range of radial positions. As a result, by passing the X-ray beam through the anatomy along a range of radial positions, while also passing the X-ray beam through the anatomy along a range of longitudinal positions, mobile CT imaging system 5 can create the desired computer model of the scanned anatomy. Significantly, with mobile CT imaging system 5, scanning is conducted while the patient remains stationary and the CT imaging system is moved, as will hereinafter be discussed in further detail.

The various electronic hardware and software for controlling the operation of X-ray tube assembly 25, X-ray detector assembly 30, and rotating drum assembly 35, as well as for processing the acquired scan data so as to generate the desired computer model, may be of the sort well known in the art and may be located in torus 10 and/or base 15.

Still looking now at FIG. 5, base 15 comprises a transport assembly 50 for moving mobile CT imaging system 5 about relative to the patient. More particularly, as disclosed in the aforementioned U.S. patent application Ser. No. 11/193,941, which patent application is hereby incorporated herein by reference, transport assembly 50 preferably comprises (i) a gross movement mechanism 55 for moving mobile CT imaging system 5 relatively quickly across room distances, so that the mobile CT imaging system can be quickly and easily brought to the patient, and (ii) a fine movement mechanism 60 for moving the mobile CT imaging system precisely, relative to the patient, during scanning, so that the patient can be scanned without being moved. As discussed in detail in the aforementioned U.S. patent application Ser. No. 11/193,941, gross movement mechanism 55 preferably comprises a plurality of free-rolling casters, and fine movement mechanism 60 preferably comprises a plurality of centipede belt drives (which can be configured for either stepped or continuous motion, whereby to provide either stepped or continuous scanning). Hydraulic apparatus 65 permits either gross movement mechanism 55 or fine movement mechanism 60 to be engaged with the floor, whereby to facilitate appropriate movement of the mobile CT imaging system 5. However, as also discussed in detail in the aforementioned U.S. patent application Ser. No. 11/193,941, gross movement mechanism 55 may be omitted entirely, and only fine movement mechanism 60 may be provided, in which case fine movement mechanism 60 is used to both (i) move mobile CT imaging system 5 to the patient prior to scanning, and (ii) move the mobile CT imaging system relative to the patient during scanning.

Base 15 preferably also includes other system components in addition to those discussed above, e.g., batteries 70 for powering the electrical components of CT machine 5, etc.

The various components of CT imaging system 5 are engineered so as to provide a relatively small, mobile and inexpensive CT imaging system. Among other things, and as will hereinafter be discussed in further detail, mobile CT imaging system 5 is sized so that its center opening 20 is just large enough to receive the head of a patient. This permits the CT imaging system to be considerably smaller in size, thereby facilitating its mobility.

As noted above, if CT imaging system 5 utilized a conventional, "on-center" x-ray beam configuration, such a size reduction would result in only the top half of the head being scanned, since the patient's shoulders would prevent the lower half of the head from reaching the mid-point of the depth of rotating drum assembly 35, i.e., from passing through the X-ray beam.

The present invention overcomes this problem by providing a novel approach for positioning the X-ray tube assembly and the X-ray detector assembly within the CT imaging system, so as to permit scanning substantially the full range of the anatomy placed within the center opening of the CT imaging system. As a result, the mobile CT imaging system can have a center opening just large enough to receive the head of a patient, yet permits scanning of the entire head of a patient.

Figure 6:
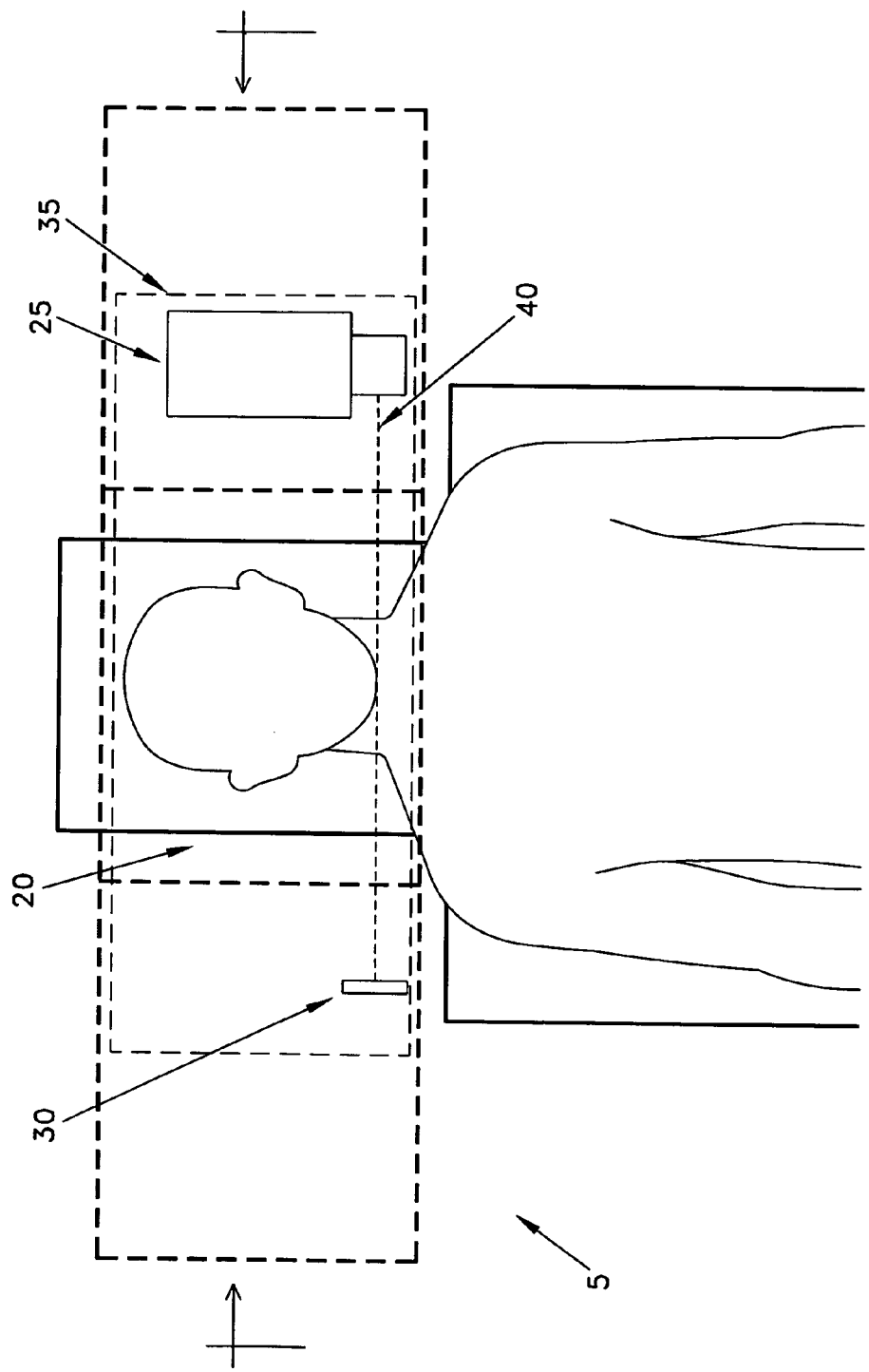
FIG. 6 is a schematic top view of the novel CT imaging system shown in FIGS. 3-5.

More particularly, as seen in FIG. 6, and as will hereinafter be discussed in further detail, the present invention provides a novel mobile CT imaging system utilizing an "off-center" x-ray beam configuration, with the X-ray beam being positioned adjacent to the entrance of the center opening of the CT imaging system. This construction permits the CT imaging system to be constructed with a center opening just large enough to receive the head of a patient, yet permits scanning of the entire head of a patient. As a result, a mobile CT imaging system can be provided with a greatly reduced size, but which also permits scanning of the full head of the patient.

Off-Center X-Ray Beam Construction

As noted above, and looking now at FIGS. 6 and 7, mobile CT imaging system 5 comprises X-ray tube assembly 25, X-ray detector assembly 30, and rotating drum assembly 35, wherein X-ray beam 40 is positioned "off-center" relative to the depth of the center opening of the CT imaging system, with the X-ray beam being positioned adjacent to the entrance of the center opening of the CT imaging system.

Figure 7:
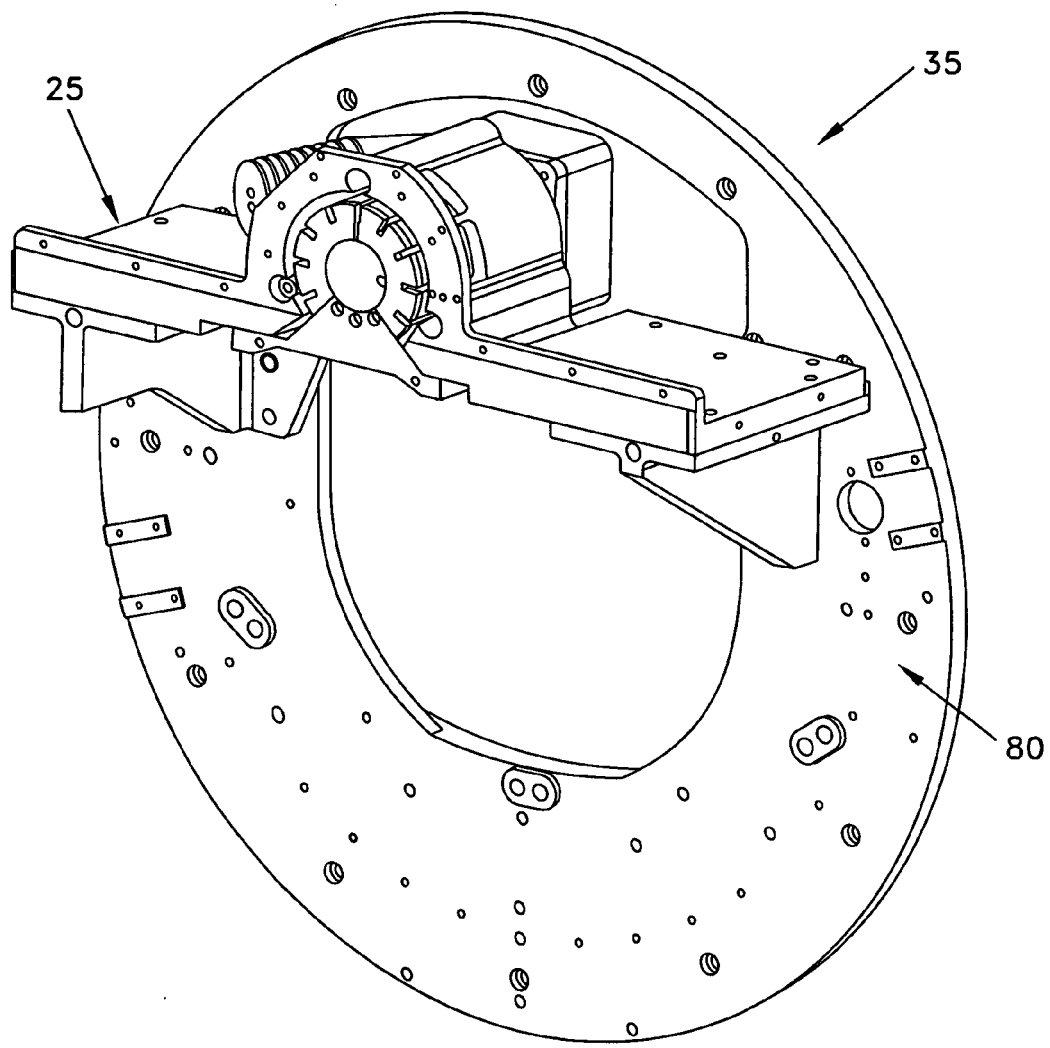
FIGS. 7 and 8 are schematic views showing the X-ray tube assembly and rotating drum assembly of the novel CT imaging system in FIGS. 3-5.
Figure 8:
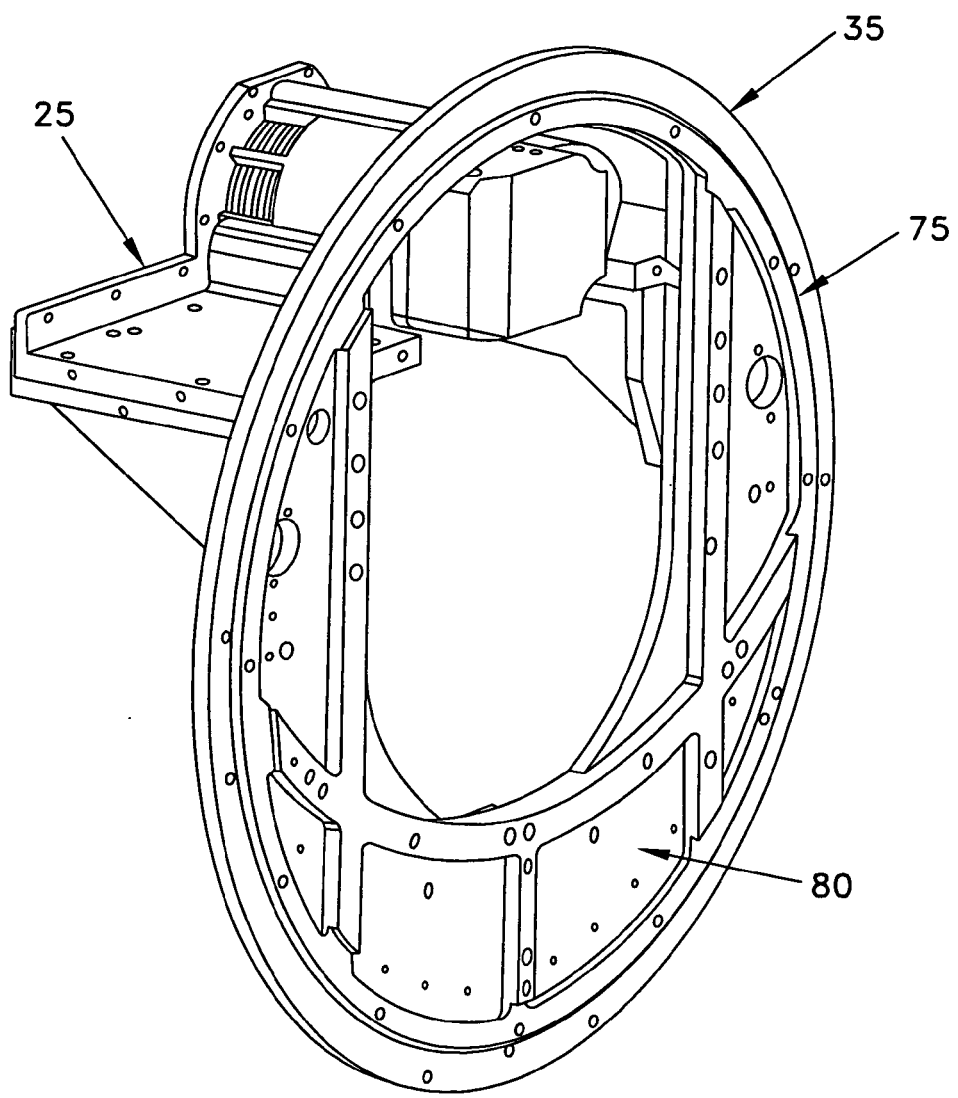
Figure 9:
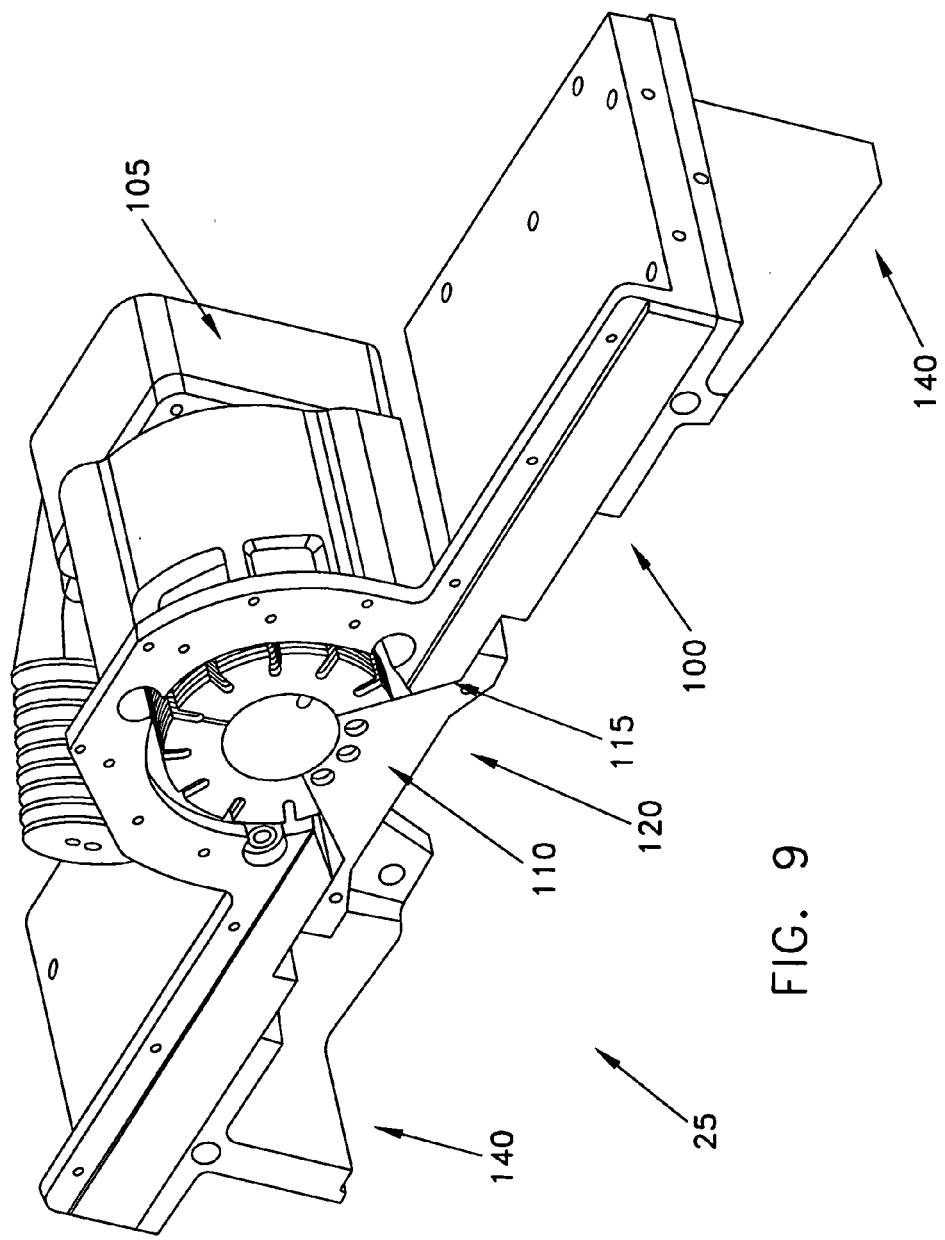
FIGS. 9-11 are schematic views of the X-ray tube assembly shown in FIG. 7.
Figure 10:
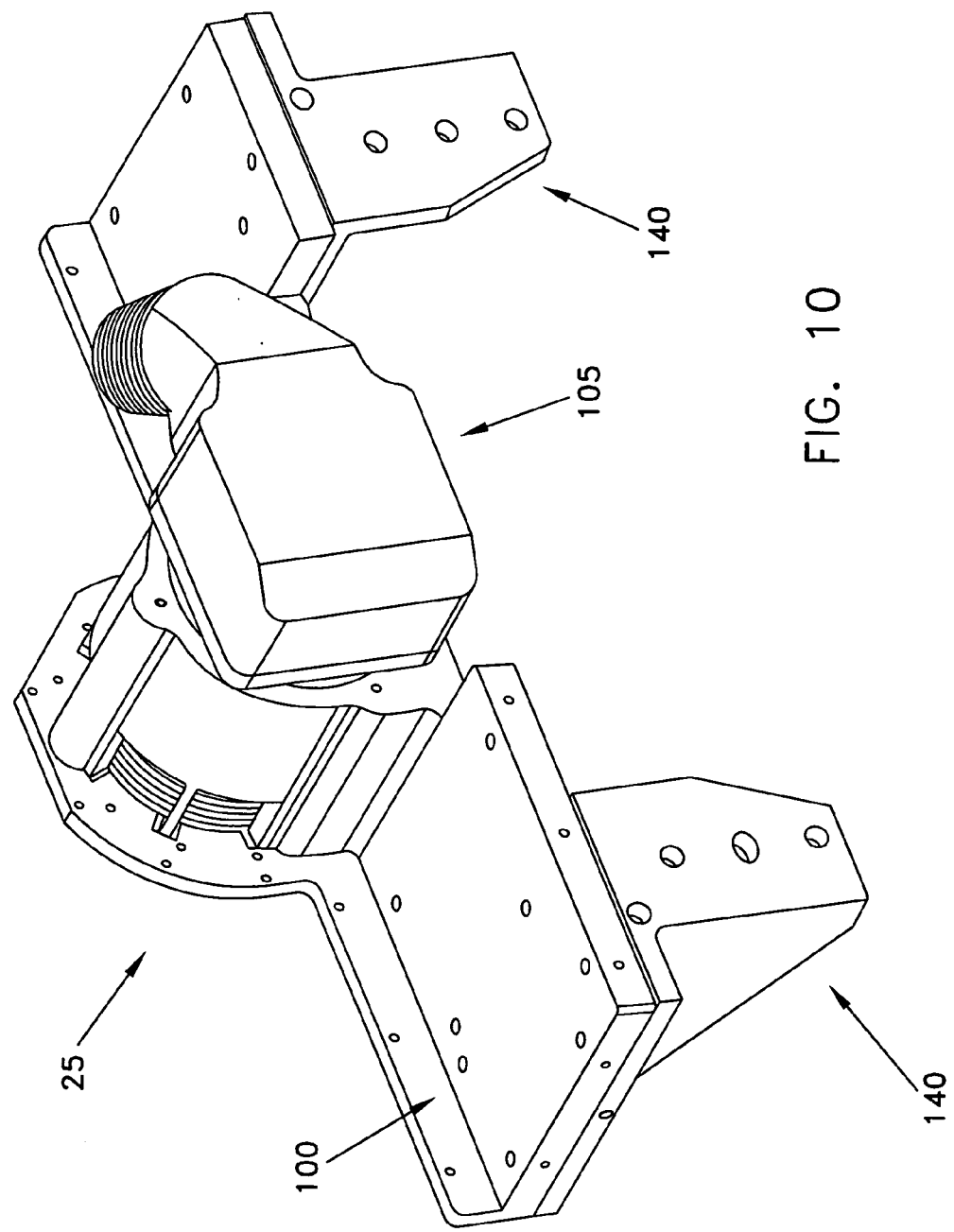
Figure 11:
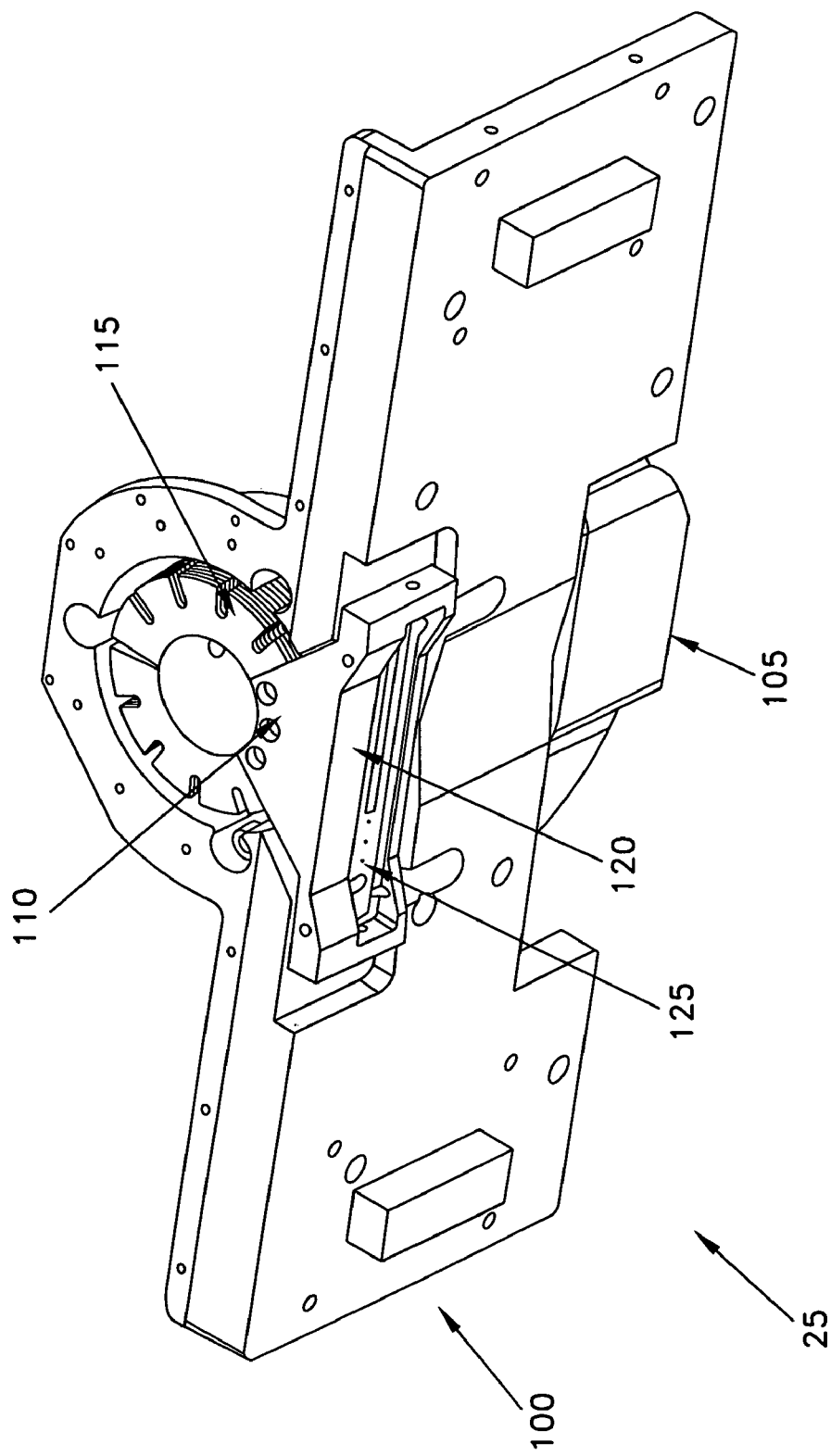
Figure 12:
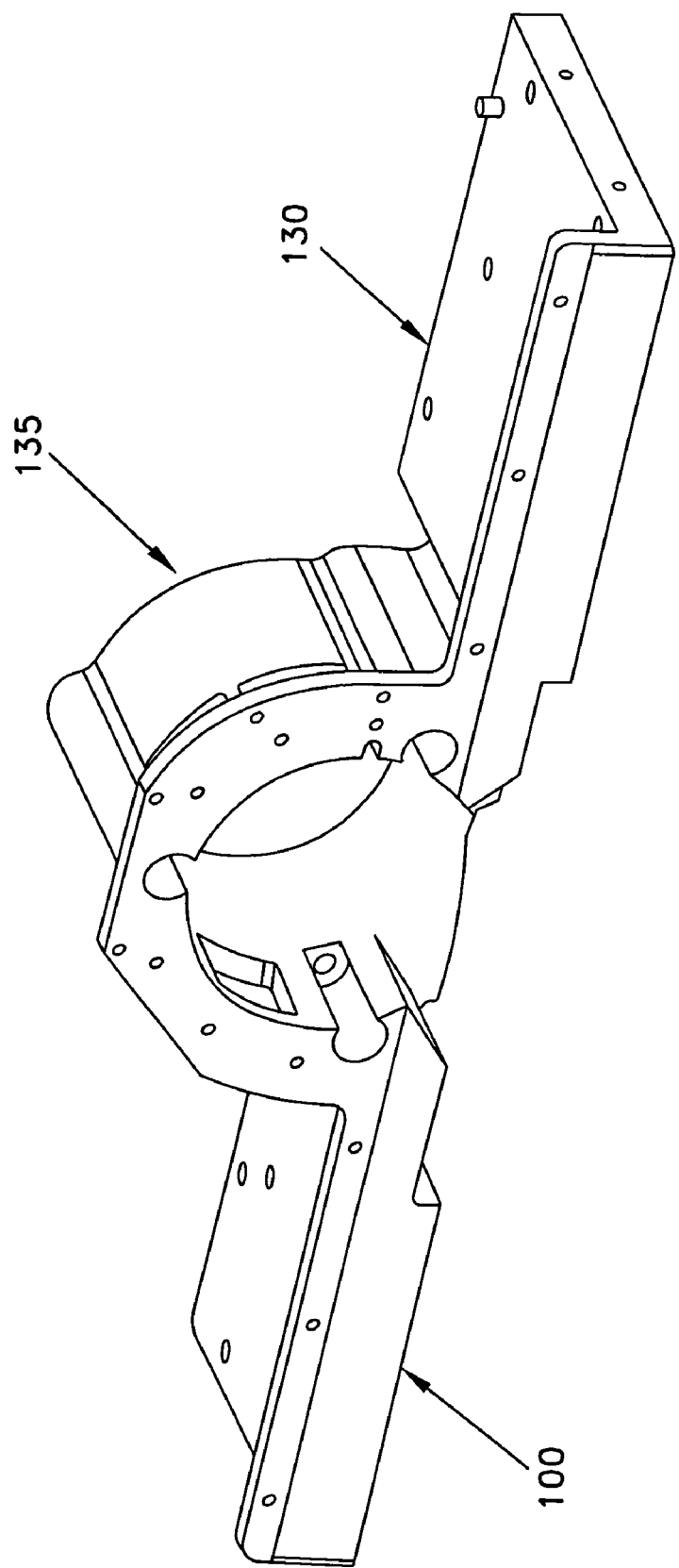
FIGS. 12 and 13 are schematic views showing the mount of the X-ray tube assembly shown in FIG. 7.
Figure 13:
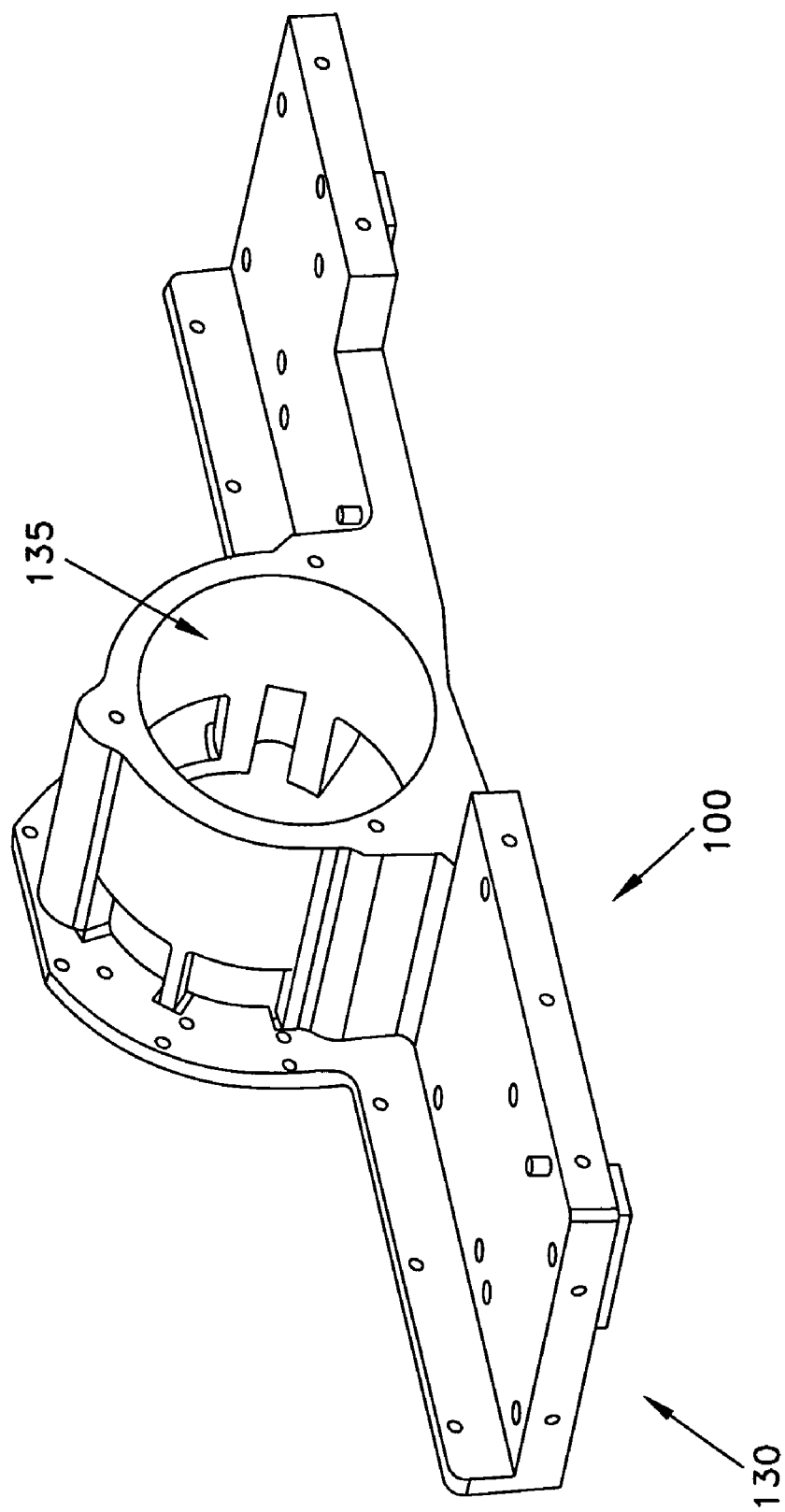
Figure 14:
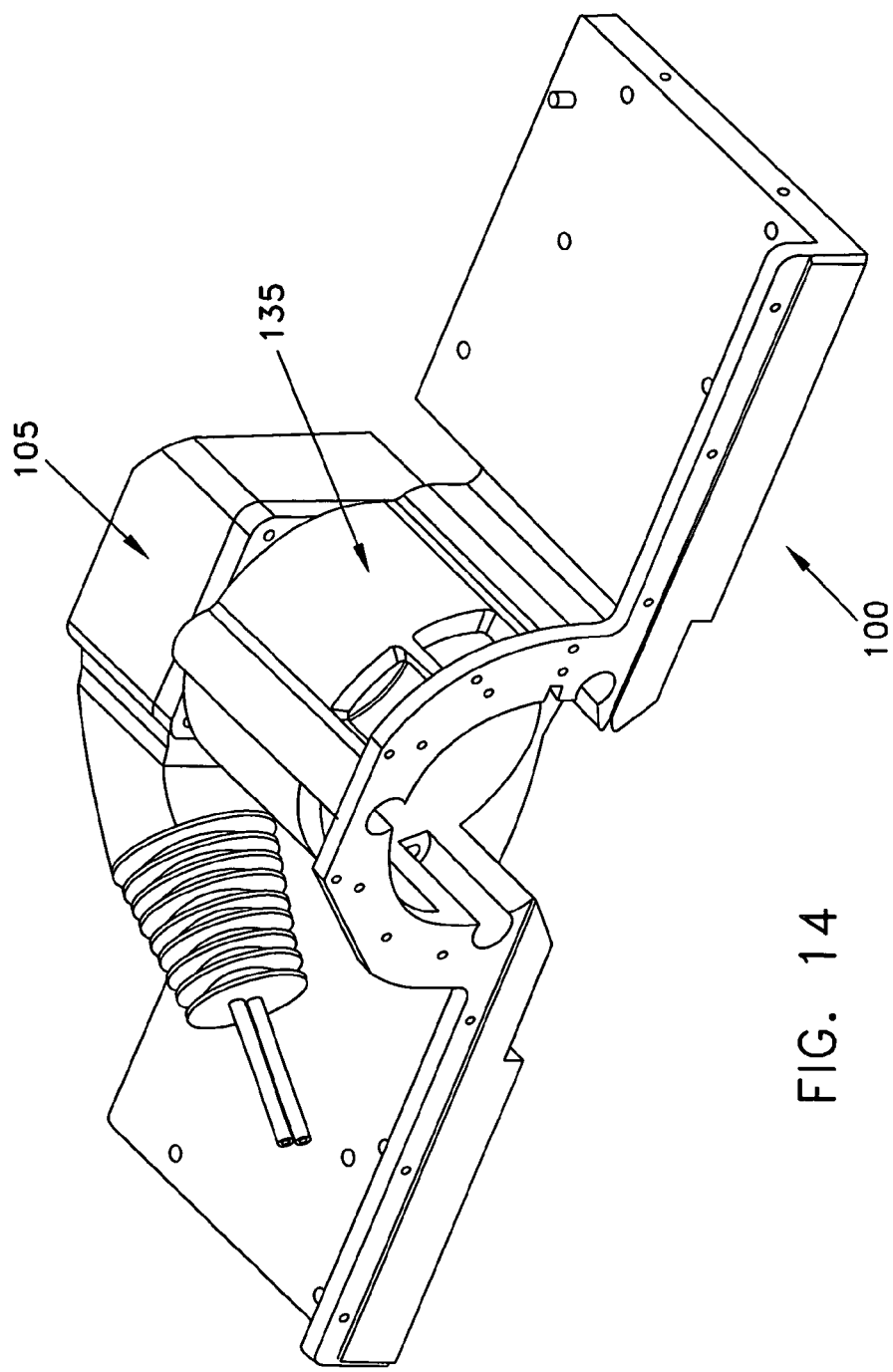
FIGS. 14-16 are schematic views showing the mount and the power connector of the X-ray tube assembly shown in FIG. 7.
Figure 15:
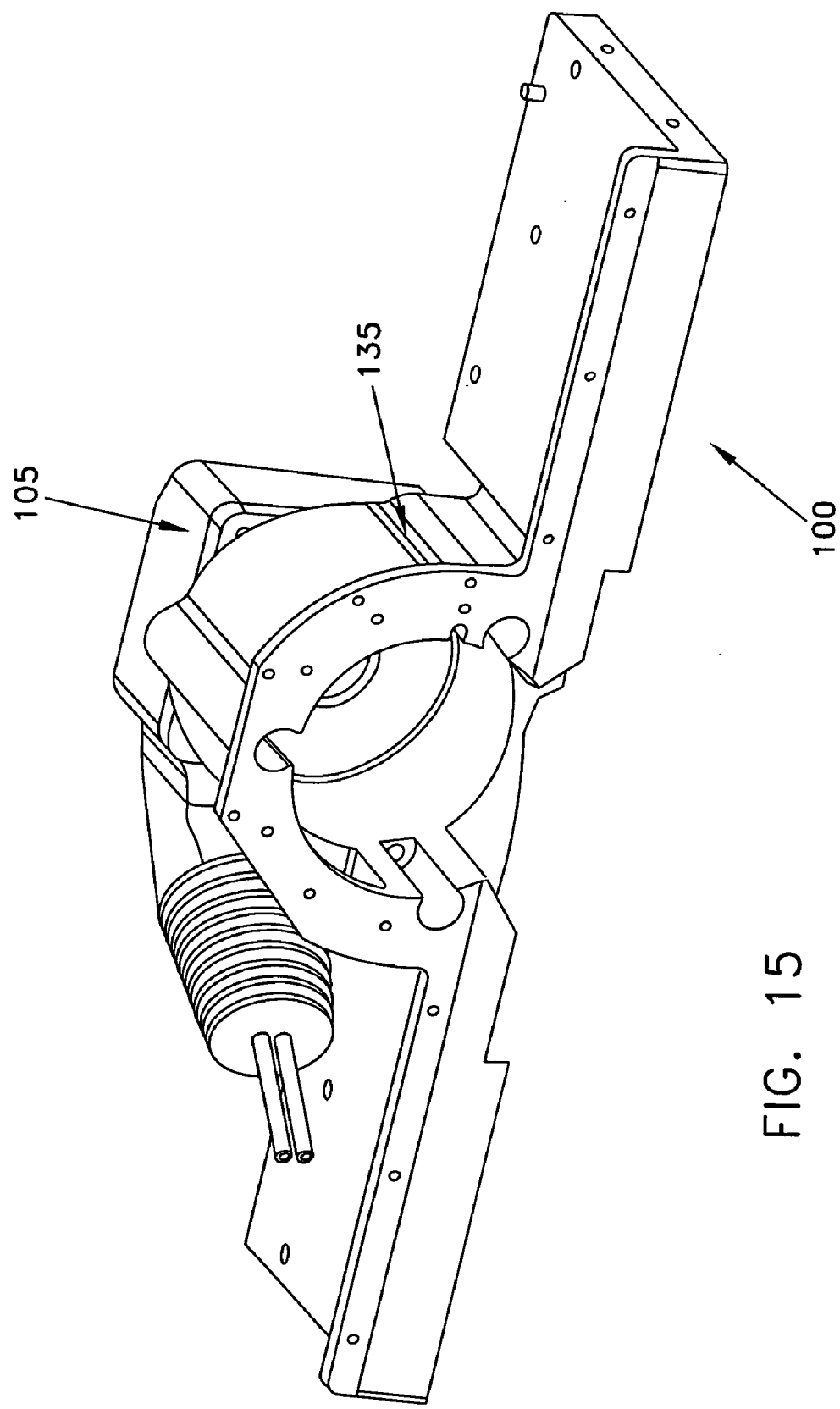
Figure 16:
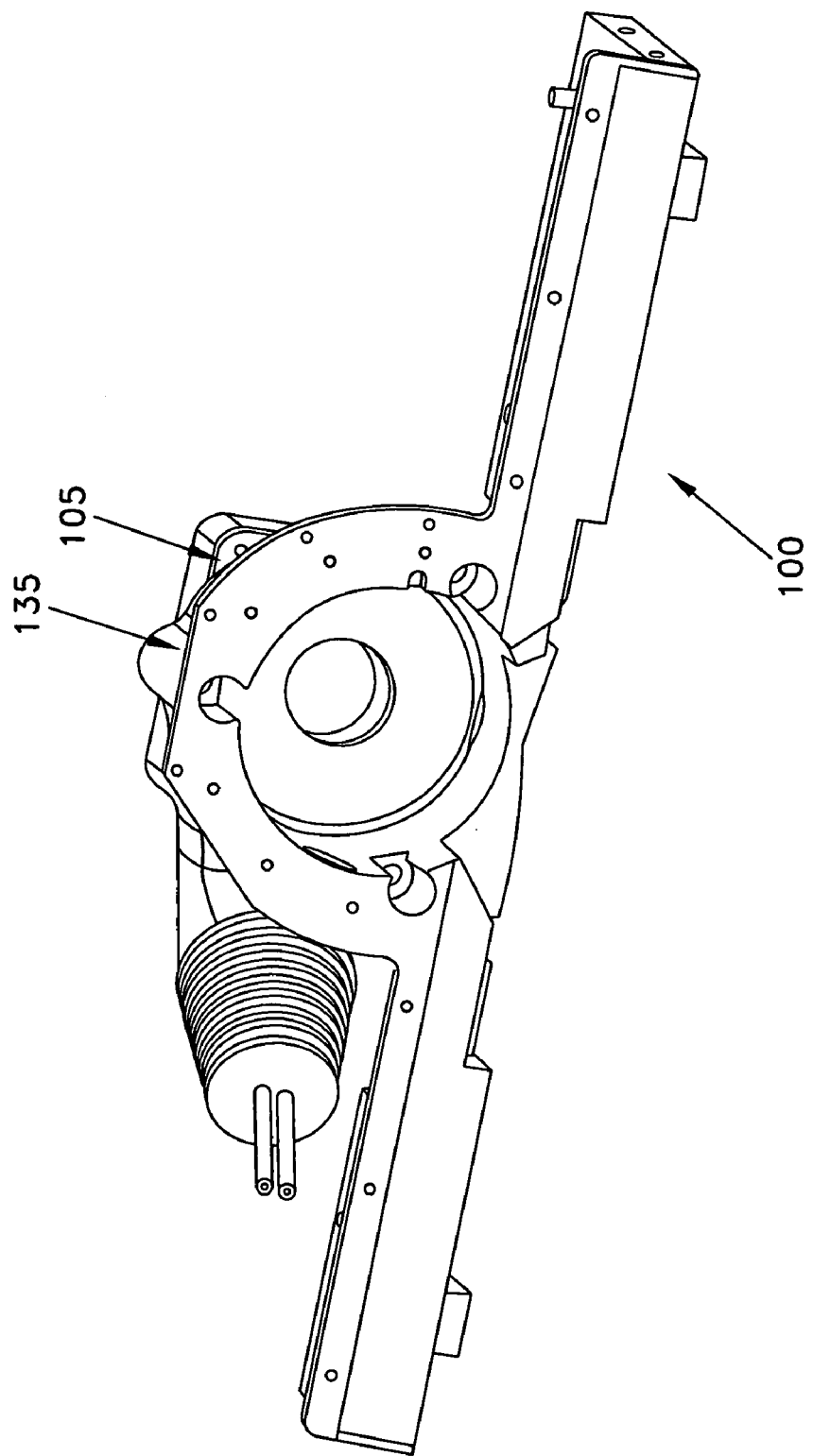

Looking now at FIGS. 7 and 8, X-ray tube assembly 25 and rotating drum assembly 35 are shown. Rotating drum assembly 35 comprises an annular drum 75 (FIG. 8). A face plate 80

(FIGS. 7 and 8) is secured to the front side of annular drum 75, so that face plate 80 rotates in conjunction with annular drum 75. X-ray tube assembly 25 is mounted to face plate 80 so that X-ray tube assembly 25 also rotates in conjunction with the drum.

Looking next at FIGS. 7-11, X-ray tube assembly 25 generally comprises a mount 100 for supporting the various components of X-ray tube assembly 25 and securing those components to face plate 80; a power connector 105 for delivering power from a power source to X-ray tube assembly 25; an X-ray tube 110 for emitting X-rays; a heat sink 115 for drawing heat away from X-ray tube 110; a collimator support 120; and a collimator 125 for collimating the X-rays emitted by X-ray tube 110 and "focusing" those X-rays on X-ray detector 30 (FIG. 5). The various components of the X-ray tube assembly 25 are designed to interconnect with one another so as to collectively form a relatively compact, lightweight and inexpensive "monoblock" assembly, as shown in FIGS. 7-11 and as discussed in further detail in pending U.S. patent application Ser. No. 11/399,283, which patent application is hereby incorporated herein by reference.

More particularly, and looking now at FIGS. 9-13, mount 100 generally comprises a frame 130 which includes a canister 135 for receiving other components, as will hereinafter be discussed, and a pair of brackets 140 (FIGS. 9 and 10) for securing frame 130 to face plate 80. Additionally, and looking now at FIGS. 9-11 and 14-16, power connector 105 is attached to mount 100 so as to supply power contacts to, and close off, the rear end of canister 135.

Figure 17:
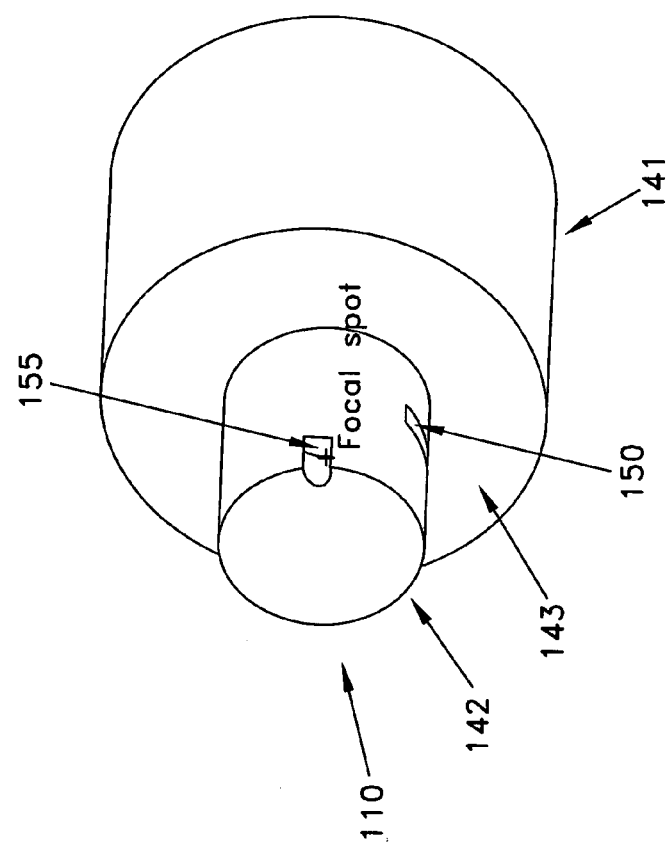
FIGS. 17 and 18 are schematic views showing the X-ray tube of the X-ray tube assembly shown in FIG. 7.
Figure 18:
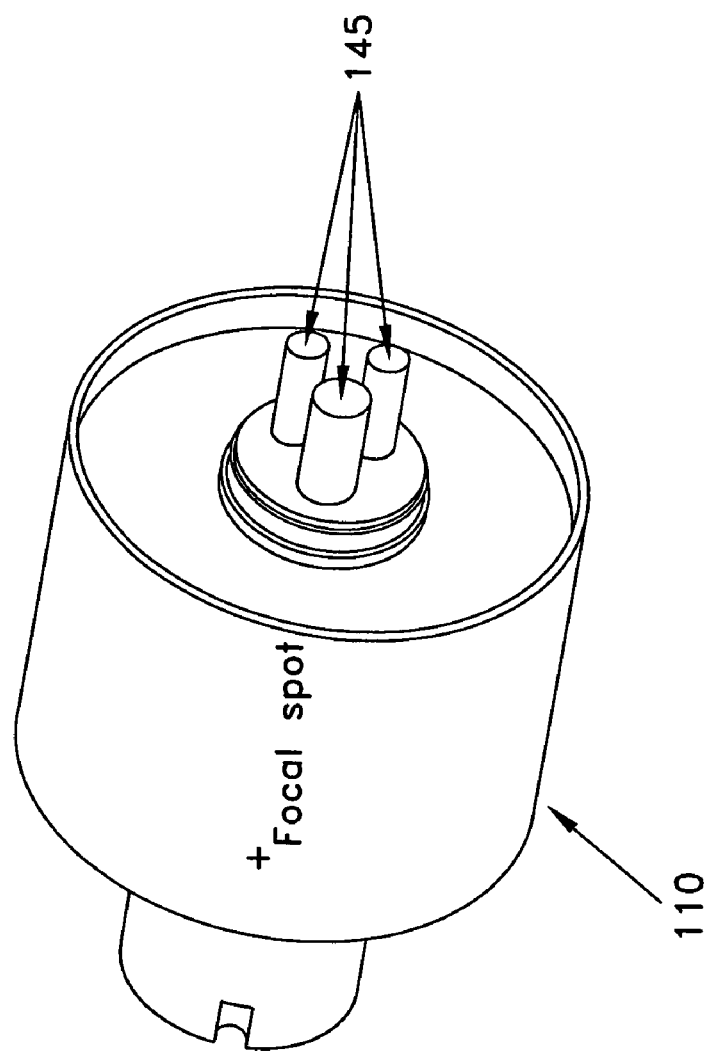

X-ray tube 110 is shown in FIGS. 17 and 18. X-ray tube 110 is preferably of the sort well known in the art of airport security scanners (e.g., it may be a RAD-12™ Rotating Anode X-ray Tube of the sort manufactured by Varian Medical Systems of Palo Alto, Calif.), and is generally characterized by a rear cylindrical portion 141, a front cylindrical portion 142, an annular face 143 formed at the intersection of rear cylindrical portion 141 and front cylindrical portion 142, rear electrical connectors 145 for delivering power to X-ray tube 110, an emitter opening 150 for emitting X-rays from the X-ray tube, and an alignment keyway 155 for use in appropriately aligning X-ray tube 110 in the X-ray tube assembly 25, as will hereinafter be discussed. While not shown in the drawings, it will be appreciated by those skilled in the art that the X-ray tube's anode is disposed in front cylindrical portion 142, adjacent to emitter opening 150.

Figure 19:
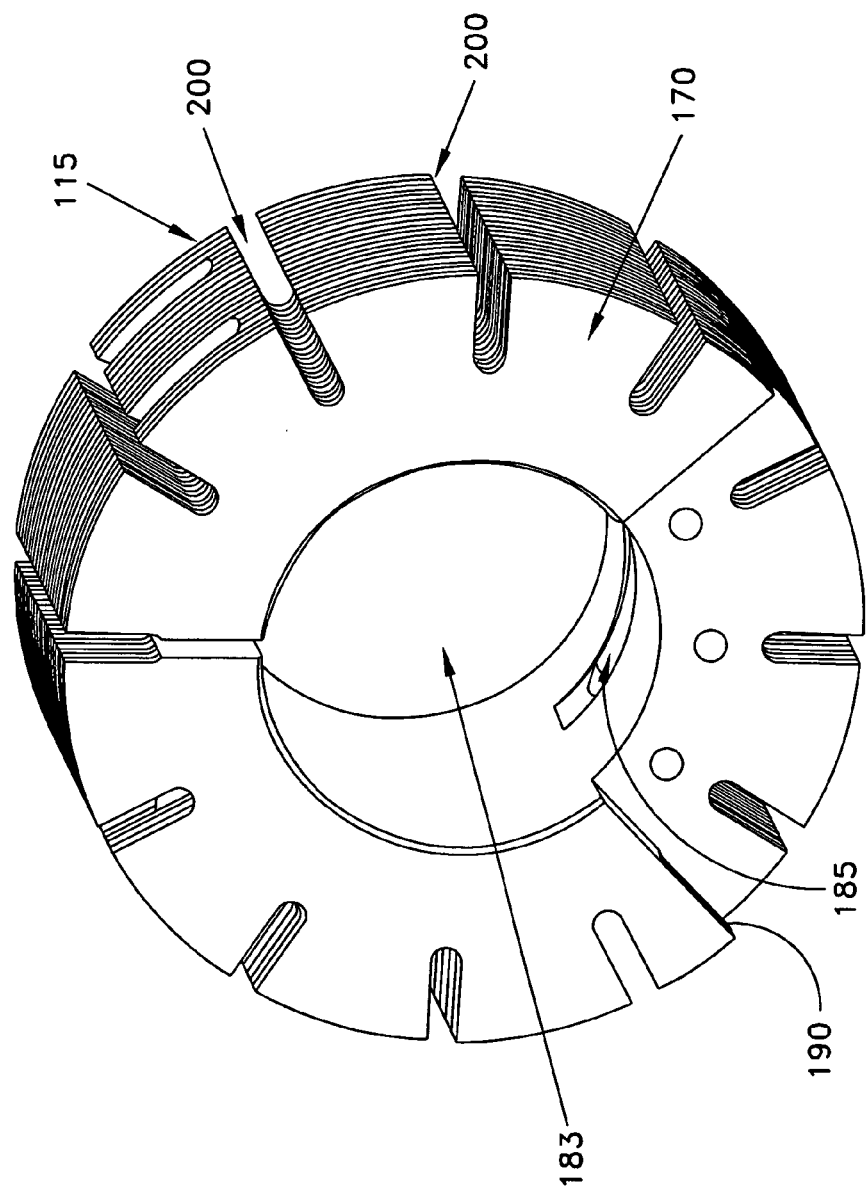
FIGS. 19 and 20 are schematic views showing various aspects of the heat sink of the X-ray tube assembly shown in FIG. 7.
Figure 20:
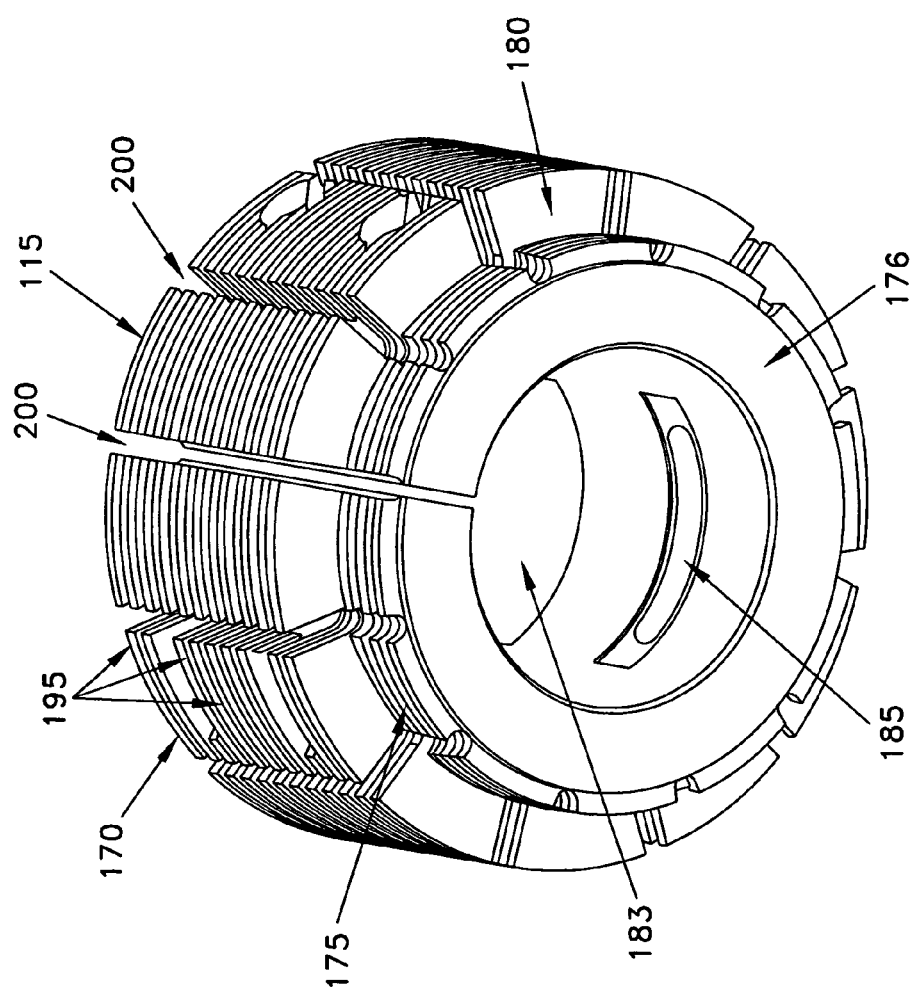

Looking next at FIGS. 19 and 20, heat sink 115 is characterized by a front cylindrical portion 170, a rear cylindrical portion 175 terminating in an end surface 176, an annular face 180 formed at the intersection of front cylindrical portion 170 and rear cylindrical portion 175, an axial opening 183 extending along the length of heat sink 115, a window 185 for passing X-rays through heat sink 115, and a front recess 190 (FIG. 19) for receiving a portion of collimator support 120, whereby to connect collimator 125 to heat sink 115, as will hereinafter be discussed. In order to increase the heat transfer capacity of heat sink 115, it is preferable to have multiple openings formed in the heat sink, whereby to increase its effective surface area. These multiple openings are preferably in the form of a plurality of circumferential slots 195, and a plurality of radial slots 200, formed in both front cylindrical portion 170 and rear cylindrical portion 175.

Figure 21:
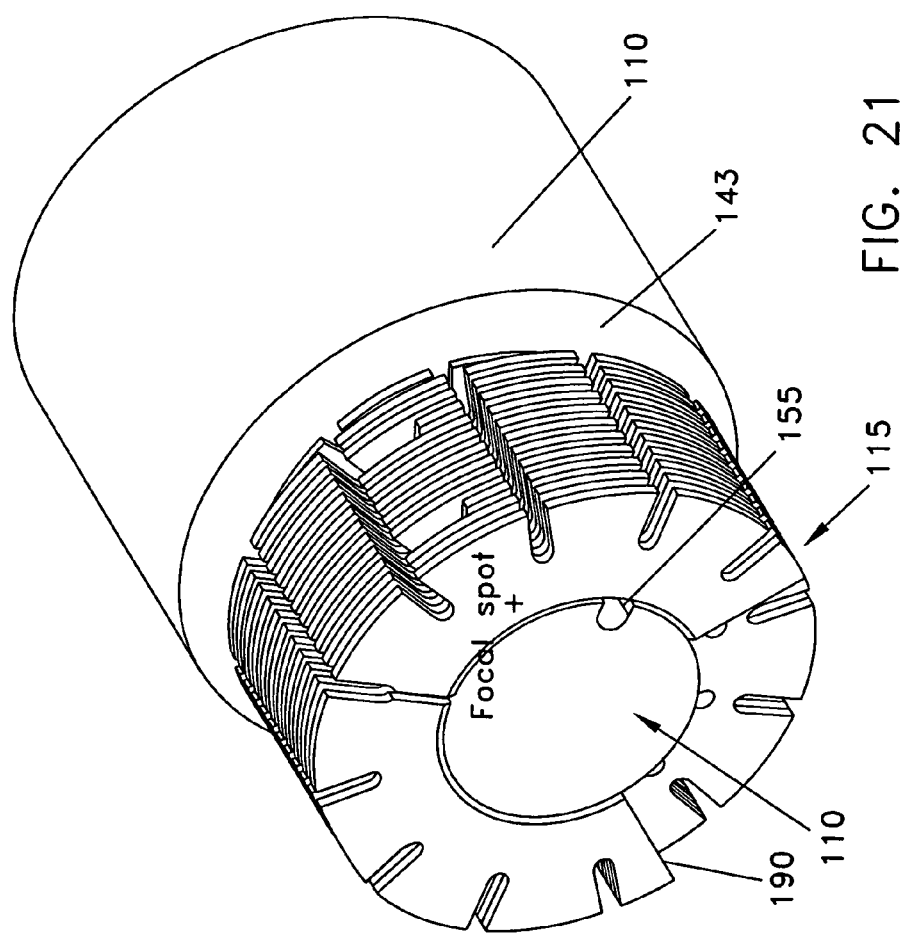
FIG. 21 is a schematic view showing the heat sink mounted to the X-ray tube.

As seen in FIG. 21, heat sink 115 is mounted onto X-ray tube 110 by seating heat sink 115 on the X-ray tube's front cylindrical portion 142, with the rear surface 176 (FIG. 20) of heat sink 115 engaging annular face 143 (FIG. 17) of the X-ray tube, and with window 185 (FIGS. 19 and 20) of heat sink 115 aligned with emitter opening 150 (FIG. 17) of X-ray tube 110. This arrangement positions the heat-conveying mass of heat sink 115 adjacent to the heat-producing anode of X-ray tube 110, and permits X-rays exiting emitter opening 150 to pass through the heat sink via window 185.

Figure 22:
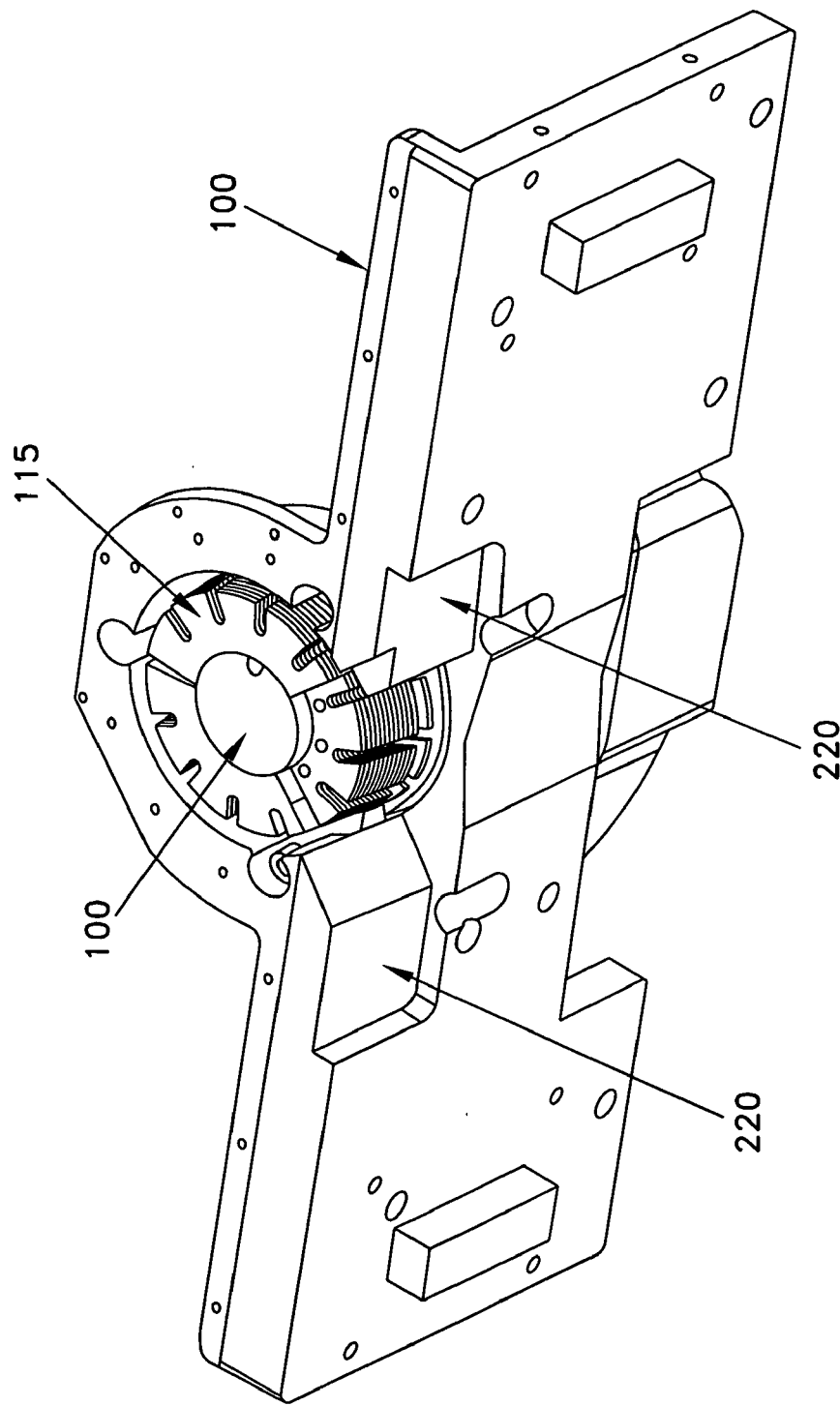
FIGS. 22-25 are schematic views showing the X-ray tube and heat sink secured to the mount and the power connector of the X-ray tube assembly shown in FIG. 7 (but with the heat sink rendered transparent in FIGS. 24 and 25 so as to reveal further aspects of the construction)
Figure 23:
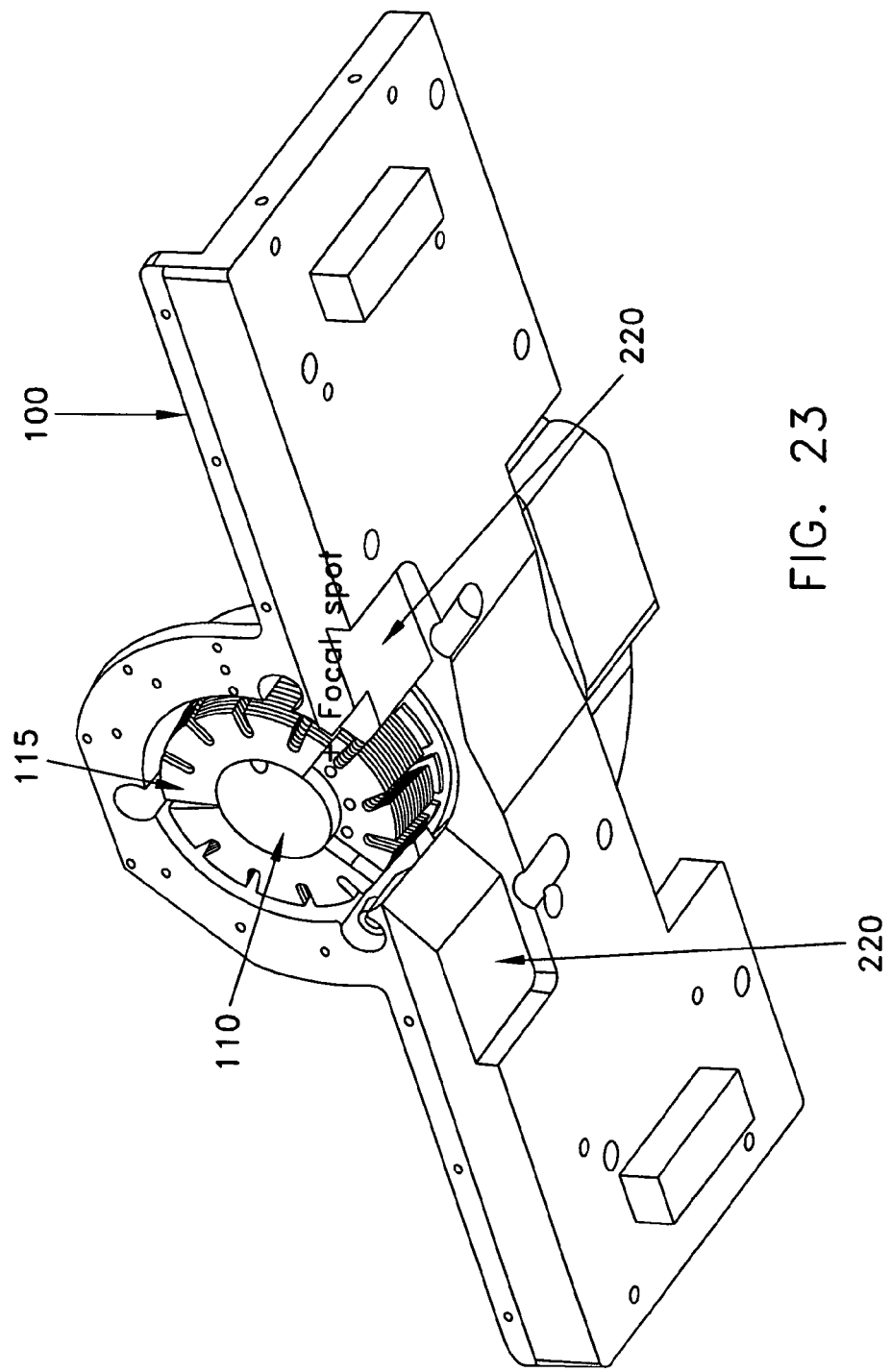
Figure 24:
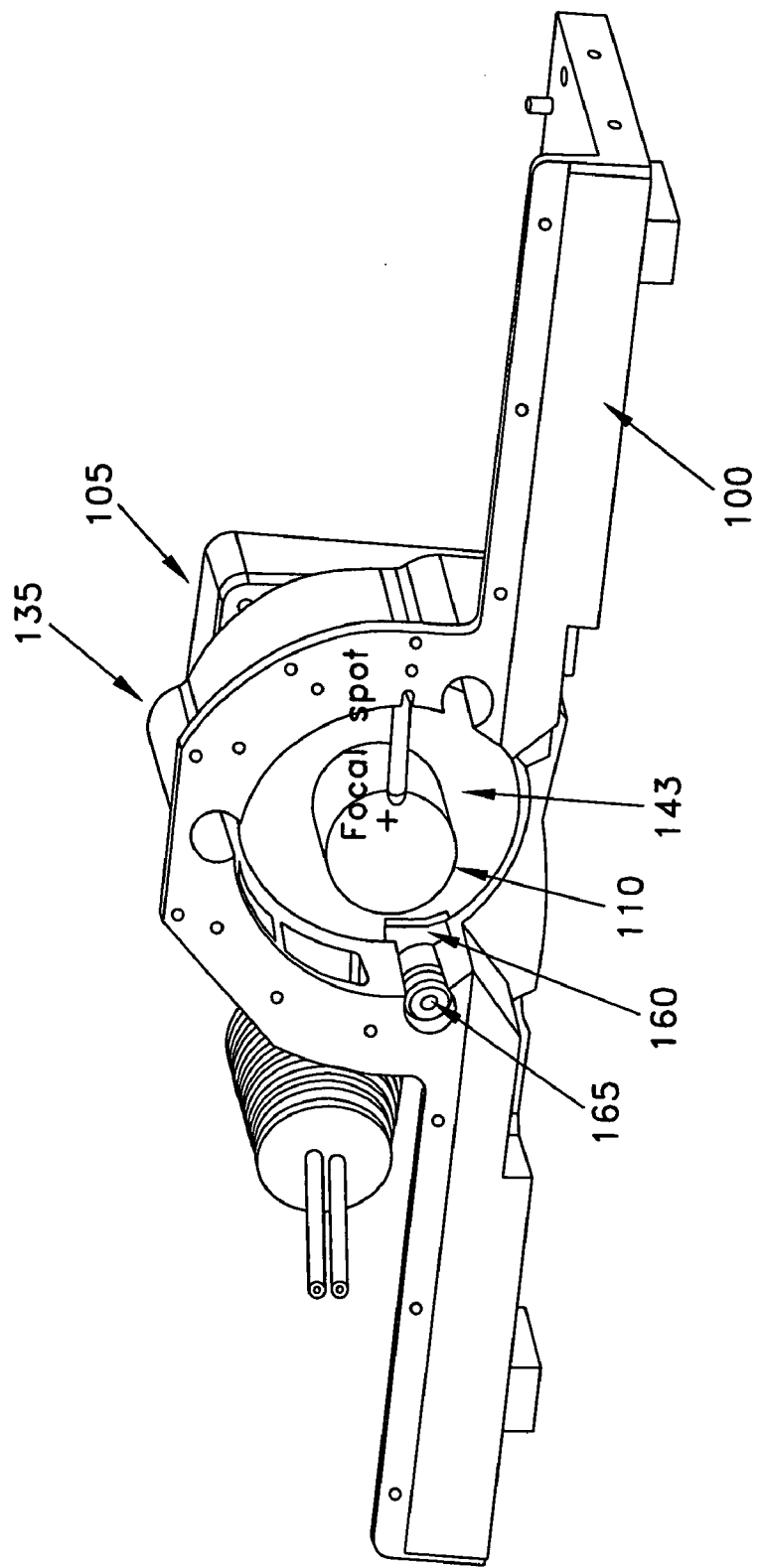
Figure 25:
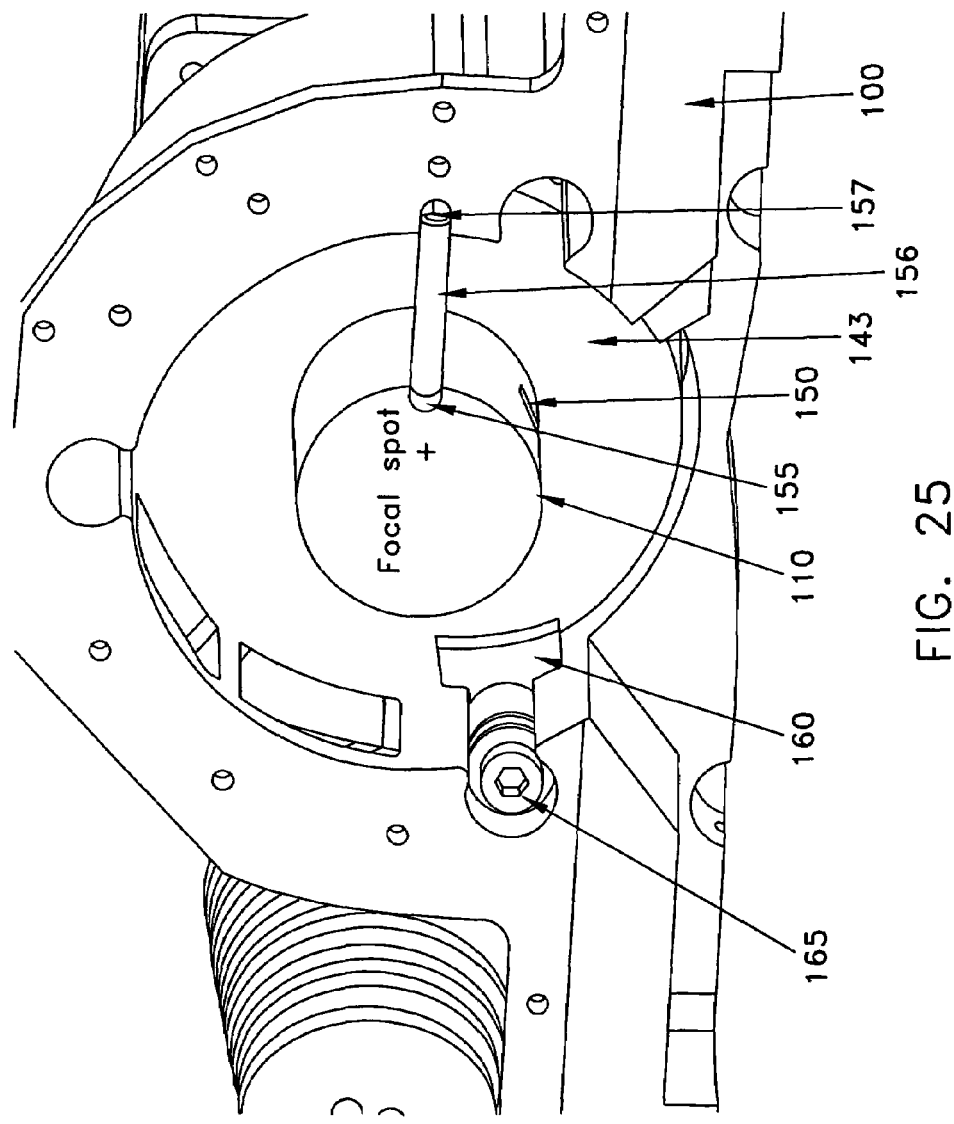
Figure 26:
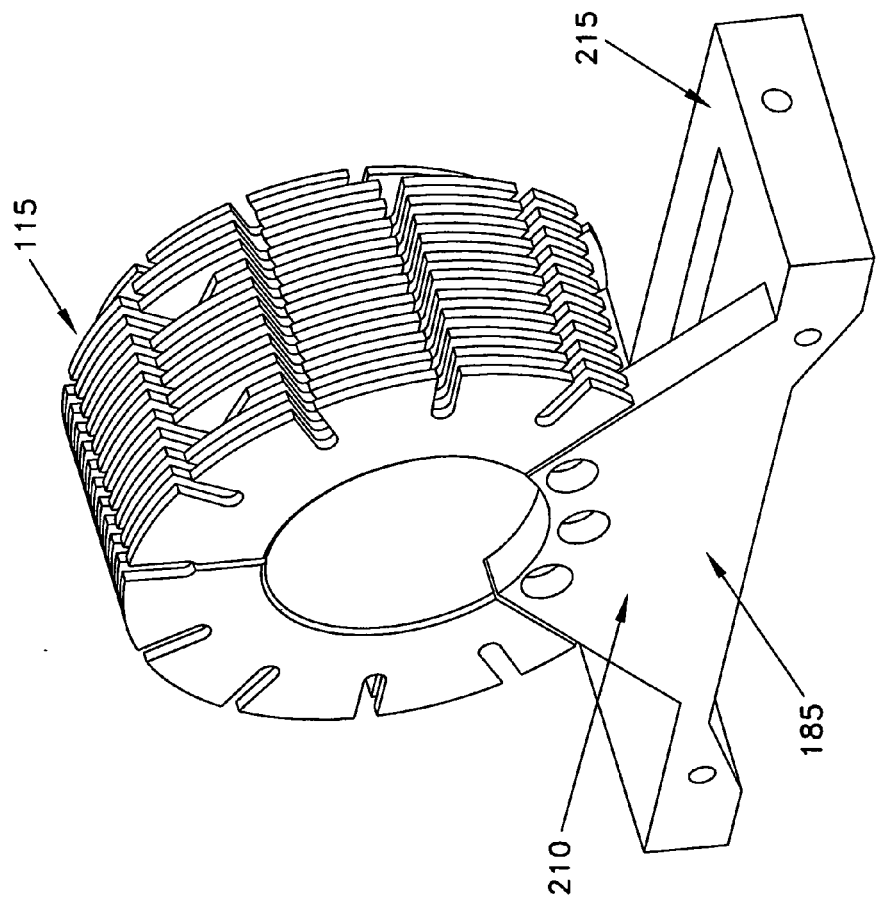
FIGS. 26-28 are schematic views showing various aspects of the collimator and the collimator support of the X-ray tube assembly shown in FIG. 7.
Figure 27:
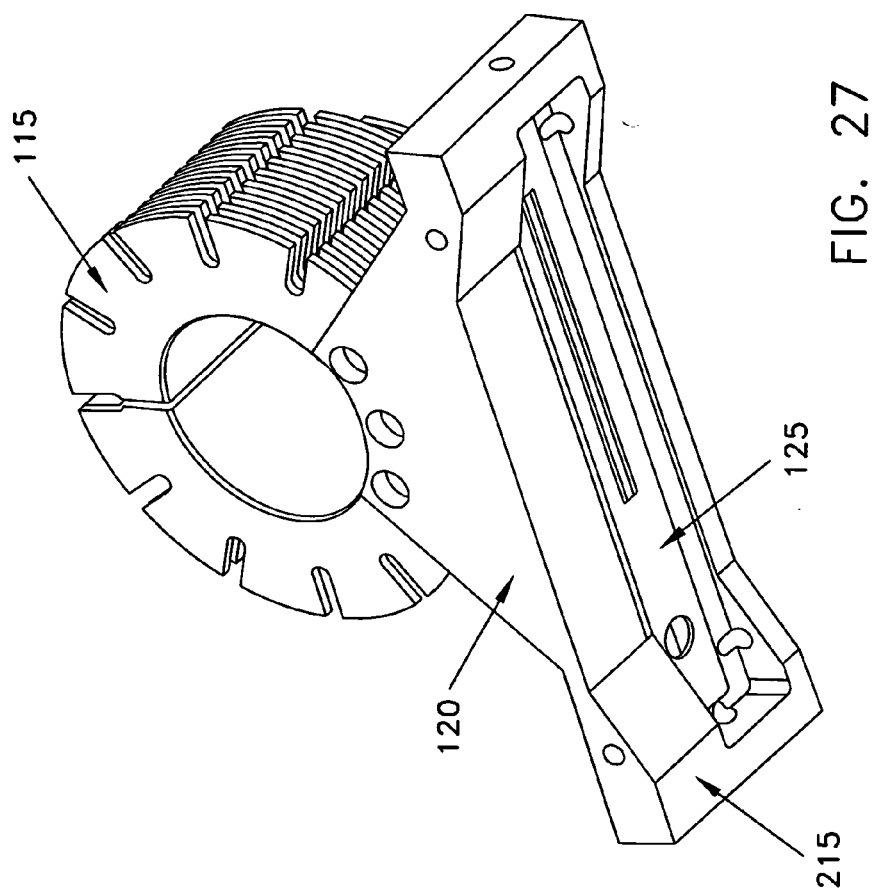
Figure 28:
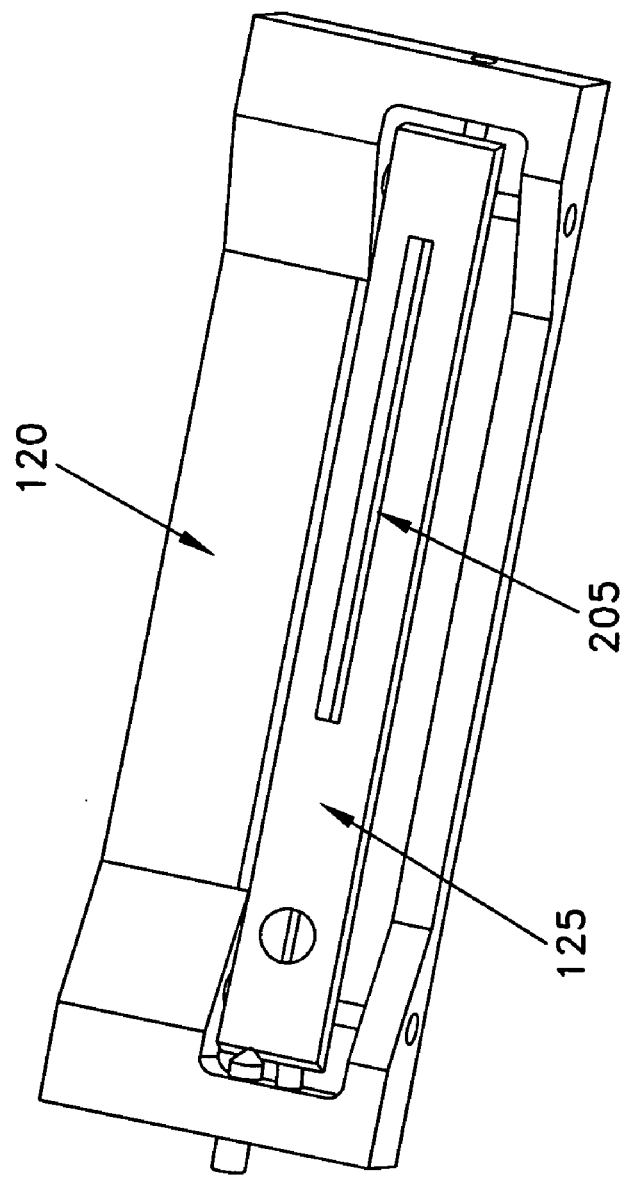

As seen in FIGS. 22 and 23, X-ray tube 110 and heat sink 115 are positioned, as a subassembly, in canister 135 so that the X-ray tube's electrical connectors 145 electrically connect to power connector 105, whereby to deliver electrical power to X-ray tube 110. As seen in FIGS. 24 and 25, which show the assembly with the heat sink rendered transparent so as to show additional construction details, an alignment pin 156 (FIG. 25) is used to align the alignment keyway 155 in X-ray tube 110 with a corresponding alignment keyway 157 formed in canister 135, whereby to ensure proper orientation of the X-ray tube relative to mount 100. A plurality of clamps 160 (FIGS. 24 and 25), secured by bolts 165, engage annular face 143 of the X-ray tube so as to secure X-ray tube 110 in position within canister 135. Preferably Belleville washers (or other spring washers) are provided to accommodate any thermal expansion of the components.

Looking next at FIGS. 9, 11, and 22-28, collimator support 120 supports collimator 125 relative to X-ray tube 100 and heat sink 115, with collimator opening 205 (FIG. 28) aligned with window 185 (FIGS. 19 and 20) of heat sink 115 (and hence with emitter opening 150 of X-ray tube 110). More particularly, an arm 210 of collimator support 120 is received in front recess 190 of heat sink 115, with a base 215 (FIGS. 26 and 27) of collimator support 120 being received in a recess 220 (FIGS. 22 and 23) of mount 100. As a result of this construction, collimator opening 205 is kept in alignment with window 185 of heat sink 115 and hence in alignment with emitter opening 150 of X-ray tube 110, so that collimator 125 may "focus" the X-rays emitted by X-ray tube 110 onto X-ray detector 30 (FIG. 5).

Heat sink 115 is preferably formed out of the same material as the anode of X-ray tube 110, such that heat sink 115 will thermally expand at the same rate as the anode of X-ray tube 110, thereby ensuring that window 185 of heat sink 115 remains in alignment with the anode of the X-ray tube 110 even if X-ray tube 110 gets hot and undergoes some thermal expansion. Furthermore, since collimator 125 is fixed to heat sink 115 via collimator support 120, collimator opening 205 remains aligned with window 185 of heat sink 115 even if thermal expansion causes some change in the position of window 185 of heat sink 115. Thus, by virtue of the foregoing construction, the emitter of X-ray tube 110 will remain in axial alignment with window 185 of heat sink 115 and opening 205 of collimator 125, regardless of any thermal expansion occurring among the parts.

Thus, in accordance with the present invention, and as shown in FIGS. 6-28, X-ray tube assembly 25, X-ray detector assembly 30, and rotating drum assembly 35 are all constructed so that X-ray beam 40 is positioned "off-center" relative to the depth of the center opening of the CT imaging system, with the X-ray beam being positioned adjacent to the entrance of the center opening of the CT imaging system. As noted above, this construction permits the entire head of the patient to be scanned, even where the center opening of the CT imaging system is sized just large enough to accommodate the head of the patient. As a result, a significantly smaller, and hence mobile, CT imaging system can be constructed.

In addition to the foregoing, since the center opening of the novel CT imaging system 5 is smaller than conventional CT imaging systems, thereby resulting in the X-ray tube assembly being positioned closer to the tissue being scanned, and since the anatomy being scanned by the novel CT imaging system 5 is thinner than the range of anatomies scanned by conventional CT imaging systems (e.g., the head of the patient versus the torso of the patient), significantly lower X-ray energies can be used with the novel CT imaging system 5. By way of example but not limitation, CT imaging system 5 can make excellent images using only 1 kW of power, versus the 36-80 kW of power normally used with conventional CT imaging systems. The use of lower X-ray energies further simplifies the creation of a small, highly mobile CT imaging system.

Use

The novel CT imaging system 5 is preferably used as follows. When a patient arrives at the emergency room presenting stroke-like symptoms, they are quickly scanned in the emergency room, on their gurney, using CT imaging system 5, which is pre-positioned in the emergency room. More particularly, CT imaging system 5 is raised on its gross movement mechanism 55, i.e., by actuating hydraulic actuators 65. CT imaging system 5 is then moved on its casters to the patient, so that the patient (while still lying on their gurney) is positioned within the center opening 20 of CT imaging system 5. As noted above, CT imaging system 5 is constructed so that center opening 20 is sized so as to be just larger than the head of the patient. Thereafter, hydraulic apparatus 65 is activated so that CT imaging system 5 is supported on its fine movement mechanism 60 (i.e., the centipede belt drives). Scanning is then commenced, with fine movement mechanism 60 precision-advancing CT imaging system 5 relative to the patient during scanning. Scanning of the full head of the patient is achieved, even though the center opening of the CT imaging machine is too small to receive the patient's shoulders, inasmuch as the CT imaging machine is provided with the "off-center" x-ray-beam configuration discussed above.

Application to Other Types of Scanning Systems

It should be appreciated that the present invention is not limited to use in medical applications or, indeed, to use with CT machines. Thus, for example, the present invention may be used in connection with CT machines used for non-medical applications, e.g., with CT machines which are used to scan inanimate objects. Furthermore, the present invention may be used with non-CT-type scanning systems.

MODIFICATIONS

It will be appreciated that still further embodiments of the present invention will be apparent to those skilled in the art in view of the present disclosure. It is to be understood that the present invention is by no means limited to the particular constructions herein disclosed and/or shown in the drawings, but also comprises any modifications or equivalents within the scope of the invention.

What is claimed is:

1. A CT imaging system comprising:
   a housing having a center opening; and
   a CT imaging unit mounted to the housing, wherein the CT imaging unit is adapted to scan anatomical objects located within the center opening and generate images of the same, wherein the CT imaging unit comprises:
   a rotatable drum assembly disposed within the housing, concentric with the center opening;
   an X-ray tube mounted on the rotatable drum assembly and configured to emit an X-ray beam; and
   an X-ray detector mounted on the rotatable drum assembly in alignment with the X-ray beam;
   wherein the X-ray beam is disposed in an "off-center" configuration, adjacent to an entrance of the center opening; and
   wherein the CT imaging system is mobile.

2. A CT imaging system according to claim 1 wherein the center opening is sized so as to be just larger than the head of a patient and smaller than the shoulders of a patient.

3. A CT imaging system according to claim 1 further comprising a transport mechanism mounted to the housing, wherein the transport mechanism comprises a fine movement mechanism for moving the CT imaging unit precisely, relative to the patient, during scanning.

4. A CT imaging system according to claim 3 wherein the fine movement mechanism is configured to move the mobile CT imaging system relative to the patient using indexed movement in discrete steps, whereby to enable slice scanning.

5. A CT imaging system according to claim 3 wherein the fine movement mechanism is configured to move the mobile CT imaging system relative to the patient using substantially continuous movement, whereby to enable helical scanning.

6. A CT imaging system according to claim 3 wherein the fine movement mechanism comprises at least one centipede belt drive unit.

7. A CT imaging system according to claim 6 wherein the fine movement mechanism comprises two centipede belt drive units.

8. A CT imaging system according to claim 7 wherein one centipede belt drive unit is disposed on either side of the patient.

9. A CT imaging system according to claim 3 wherein the transport mechanism further comprises a gross movement mechanism for transporting the mobile CT imaging system relatively quickly across room distances.

10. A CT imaging system according to claim 9 wherein the gross movement mechanism comprises at least one caster unit.

11. A CT imaging system according to claim 10 wherein the gross movement mechanism comprises two caster units, each having two caster wheels.

12. A CT imaging system according to claim 11 wherein one caster unit is disposed on either side of the patient.

13. A CT imaging system according to claim 9 wherein the transport mechanism is configured so that the mobile CT imaging system is: (i) transported by the gross movement mechanism while the mobile CT imaging system is being moved across room distances to the patient; and (ii) moved precisely relative to the patient by the fine movement mechanism while the patient is being scanned by the mobile CT imaging system.

14. A CT imaging system according to claim 9 wherein the gross movement mechanism comprises an actuator for: (i) extending portions of the gross movement mechanism below portions of the fine movement mechanism whereby the mobile CT imaging system will be supported by portions of the gross movement mechanism; and (ii) retracting portions of the gross movement mechanism above portions of the fine movement mechanism whereby the mobile CT imaging system will be supported by portions of the fine movement mechanism.

* * * * *